United States Patent
Gewirtz et al.

(10) Patent No.: US 9,872,895 B2
(45) Date of Patent: Jan. 23, 2018

(54) TLR5 LIGANDS, THERAPEUTIC METHODS, AND COMPOSITIONS RELATED THERETO

(75) Inventors: Andrew T. Gewirtz, Smyrna, GA (US); Benyue Zhang, Liburn, GA (US)

(73) Assignee: Emory University, Atlanta, GA (US)

( * ) Notice: Subject to any disclaimer, the term of this patent is extended or adjusted under 35 U.S.C. 154(b) by 63 days.

(21) Appl. No.: 13/825,349

(22) PCT Filed: Sep. 20, 2011

(86) PCT No.: PCT/US2011/052301
§ 371 (c)(1),
(2), (4) Date: Oct. 15, 2014

(87) PCT Pub. No.: WO2012/040164
PCT Pub. Date: Mar. 29, 2012

(65) Prior Publication Data
US 2015/0165009 A1 Jun. 18, 2015

Related U.S. Application Data

(60) Provisional application No. 61/386,138, filed on Sep. 24, 2010.

(51) Int. Cl.
| | | |
|---|---|---|
| *A61K 38/16* | (2006.01) | |
| *A61K 39/02* | (2006.01) | |
| *A61K 38/21* | (2006.01) | |
| *A61K 39/39* | (2006.01) | |
| *A61K 45/06* | (2006.01) | |
| *A61K 39/00* | (2006.01) | |

(52) U.S. Cl.
CPC ............ *A61K 39/02* (2013.01); *A61K 38/164* (2013.01); *A61K 38/21* (2013.01); *A61K 39/39* (2013.01); *A61K 45/06* (2013.01); *A61K 2039/58* (2013.01); *C12N 2720/12371* (2013.01)

(58) Field of Classification Search
None
See application file for complete search history.

(56) References Cited

U.S. PATENT DOCUMENTS

| 7,638,485 B2 | 12/2009 | Gudkov | |
|---|---|---|---|
| 2003/0044429 A1 | 3/2003 | Aderem | |
| 2005/0147627 A1 | 7/2005 | Aderem | |
| 2007/0298014 A1* | 12/2007 | Huang | A61K 35/74 424/93.4 |
| 2008/0124361 A1 | 5/2008 | Mizel | |
| 2009/0297552 A1* | 12/2009 | Aderem | A61K 39/39 424/192.1 |
| 2010/0104516 A1 | 4/2010 | Yu | |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Babu et al. (Appl. Microbiol. Biotechnol., 53:655-660, 2000).*
ATRIPLA™ (efavirenz 600 mg/emtricitabine 200 mg/tenofovir disoproxil fumarate 300 mg) Tablets, NDA 21-937, 2006 Bristol-Myers Squibb & Gilead Sciences.
Babu et al. "Production of interferon-alpha in high cell density cultures of recombinant *Escherichia coli* and its single step purification from refolded inclusion body proteins" Appl Microbial Biotechnol. 2000; 53(6): 655-660.
Blaising et al. "Arbidol as a broad-spectrum antiviral: An update" Antiviral Research, 2014; 107: 84-94.
Eaves-Pyles et al. "*Salmonella* Flagellin-Dependent Proinflammatory Responses are Localized to the Conserved Amino and Carboxyl Regions of the Protein" J Immunol, 2001; 167: 7009-7016.
Gargano et al. "Signaling through Toll-like receptors induces murine gammaherpesvirus 68 reactivation in vivo" J Virol., 2009; 83(3): 1474-1482.
Liaudet et al. "The Flagellin—TLR5 Axis: Therapeutic Opportunities" Drug News Perspect, Sep. 2002; 15(7): 397-409.
Mitchell et al. "The quest for effective Ebola treatment: Ebola VP35 is an evidence-based target for dsRNA drugs" Emerging Microbes and Infections, 2014; 3: e77.
Smith et al. "Toll-like receptor 5 recognizes a conserved site on flagellin required for protofilament formation and bacterial motility" Nature Immunology, 2003; 4: 1247-1253.
Thibault et al. "TLR5 stimulation is sufficient to trigger reactivation of latent HIV-1 provirus in T lymphoid cells and activate virus gene expression in central memory CD4+ T cells" Virology, 2009; 389: 20-25.
TRIZIVIR® (abacavir sulfate, lamivudine, and zidovudine) Prescribing Information 2009, GlaxoSmithKline.
TRUVADA® (emtricitabine/tenofovir disoproxil fumarate) tablets, for oral use, Initial U.S. Approval: 2004.
Vijay-Kumar et al. "Flagellin Treatment Protects against Chemicals, Bacteria, Viruses, and Radiation" J Immunol., 2008; 180(12): 8280-8285.
Zeng et al. "Flagellin/TLR5 responses in epithelia reveal intertwined activation of inflammatory and apoptotic pathways" Am J Physiol Gastrointest Liver Physiol, 2006; 290: G96-G108.
Zhang et al. "Prevention and cure of rotavirus infection via TLR5/NLRC4-mediated production of IL-22 and IL-18" Science, 2014; 346(6211): 861-865.

\* cited by examiner

*Primary Examiner* — Brian J Gangle
(74) *Attorney, Agent, or Firm* — Emory Patent Group

(57) ABSTRACT

The disclosure relates to antiviral therapeutic methods and related compositions. In certain embodiments, the disclosure relates to methods of treating or preventing a viral infection by administering a pharmaceutical composition comprising a TLR5 ligand, such as a flagellin, to a subject in need thereof.

16 Claims, 15 Drawing Sheets

TLR5 LIGANDS, THERAPEUTIC METHODS, AND COMPOSITIONS RELATED THERETO

CROSS REFERENCE TO RELATED APPLICATIONS

This application is the National Stage of International PCT Application Number PCT/US2011/052301 filed Mar. 21, 2011, which claims priority to U.S. Provisional Application No. 61/386,138 filed Sep. 24, 2010, all of which are hereby incorporated by reference in their entireties.

ACKNOWLEDGEMENTS

This invention was made with government support under Grant R01 DK061417 awarded by the National Institutes of Health. The government has certain rights in the invention.

FIELD

The disclosure relates to antiviral therapeutic methods and related compositions. In certain embodiments, the disclosure relates to methods of treating or preventing a viral infection by administering a pharmaceutical composition comprising a TLR5 ligand, such as a flagellin, to a subject in need thereof.

BACKGROUND

The World Health Organization estimates that AIDS has killed more than 25 million people since it was first recognized. In 2007 there were 2.7 million new HIV infections and 2 million HIV-related deaths. Many chronic infections are retroviruses. Anti-retroviral drugs are medications for the treatment of infection by retroviruses such as HIV. When several agents are taken in combination, the approach is known as highly active antiretroviral therapy (HAART). HAART can have serious side-effects. Regimens can be complicated, requiring patients to take several pills at various times during the day. If patients miss doses, drug resistance can develop. Therefore, there remains a need for improved antiviral therapies. In particular, there remains a need for antiviral therapies with reduced toxicity and improved efficacy over existing treatments.

For certain chronic viral infections, the immune system cannot clear the virus from the host even with the aid of therapeutic agents. For example, although HAAT may improve symptoms associated with infection, there is currently no cure for HIV. Toll-like receptors (TLRs) play a role in the pathogenesis of multiple diseases involving both the innate and adaptive immune systems. TLRs in humans recognize different microbial ligands during infection. There are several protein kinases downstream of these adapters, notably the IL-1 receptor-associated kinase (IRAK) family and TBK-1. These activate pathways leading to the activation of the respective transcription factors nuclear factor kappaB (NFκB) and interferon regulatory factor 3 (IRF3), which in turn induce various immune and inflammatory genes.

TLR5 is the receptor for bacterial flagellin monomers. The region of flagellin that TLR5 recognizes is conserved among microbial species and therefore allows TLR5 to detect a wide variety of microbes. TLR5 signals by recruiting the TIR adapter MyD88, leading to the activation of the IKK complex and subsequent activation of the transcription factor NFκB. The activation of TLR5 has been recently reported to be an efficient adjuvant for influenza A vaccines. See, e.g., U.S. Published Patent Application No. 2005/0147627 (flagellin contemplated in vaccine adjuvant). Studies indicate that activating the TLR5 signaling pathway may have other therapeutic applications, not only in its role as a linker adjuvant candidate for vaccines, but also as a dampener of excessive apoptosis in acute radiation syndromes, a characteristic that may be extended for use in degenerative diseases and ischemia reperfusion injury. See, e.g., U.S. Pat. No. 7,638,485. It has been suggested that systemic administration of flagellin may protect against chemicals, bacteria, viruses, and radiation. Vijay-Kumar et al., J Immunol. 2008, 180(12):8280-5. It has also been identified that flagellin reactivates gene expression in certain viruses. See, e.g., Gargano et al., J Virol, (2009), 83(3):1474-82 and Thibault et al., Virology (2009) 389 (1-2): 20-5.

SUMMARY

Although flagellin is derived from flagellated bacteria, it has been discovered that administering flagellin to a subject can be used to treat certain viral infections. The disclosure relates to the use of a flagellin or other TLR5 ligands in antiviral therapeutic methods and related compositions.

In some embodiments, the disclosure relates to methods of treating a viral infection in a subject, comprising administering a composition comprising a TLR5 ligand to a subject that is diagnosed with, suspected of, or exhibiting symptoms of a viral infection. In certain embodiments, the composition is administered post-infection. In certain embodiments, the TLR5 ligand is a flagellin protein, or a fragment or derivative thereof. In specific embodiments, the TLR5 ligand is a flagellin. In some embodiments, the subject is diagnosed with a chronic viral infection. In certain embodiments, the subject undergoes serological monitoring. In some embodiments, the administration is under conditions such that the viral infection is no longer detected. In some embodiments, the subject is diagnosed with a RNA virus, DNA virus, or retroviruses. In some embodiments, the subject is diagnosed with a virus that is a double stranded DNA virus, sense single stranded DNA virus, double stranded RNA virus, sense single stranded RNA virus, antisense single stranded RNA virus, sense single stranded RNA retrovirus or a double stranded DNA retrovirus. In some embodiments, the subject is diagnosed to have a rotavirus, an influenza virus, a herpes virus, a hepatitis virus, or a lentivirus. In some embodiments, titer of the virus in the subject is reduced after the treatment as compared to pre-treatment.

In certain embodiments, the subject is a mammal, typically a human.

In certain embodiments, the disclosure relates to methods of treating a subject diagnosed with a viral infection or preventing a viral infection by administration of a TLR5 ligand, typically flagellin, wherein the subject is immunocompromised. In typical embodiments, the subject is an organ transplant recipient, undergoing hemodialysis, diagnosed with cancer, receiving an immunosuppressive drug, and/or diagnosed with an HIV-infection. In certain embodiments, the disclosure relates to preventing a viral infection in an immunocompromised subject at risk of infection by administering a TLR5 ligand, typically flagellin, and optionally one or more antiviral agents. In certain embodiments, the subject is at risk of an infection because the sexual partner of the subject is diagnosed with a virus. In certain embodiments, flagellin is administered for prophylactic use, not provided as a vaccine, administered for at least a 1 hour, 4 hours, 1 day, 2 days, 3 days, 1 week, or 1 month before a subject may be at risk of an infection.

In some embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In some embodiments, the disclosure relates to treating chronic tuberculosis by administering a flagellin to a subject diagnosed with tuberculosis. In some embodiments, flagellin is administered in combination with another antibiotic.

In some embodiments, the subject is diagnosed with gastroenteritis, acute respiratory disease, severe acute respiratory syndrome, post-viral fatigue syndrome, viral hemorrhagic fevers, acquired immunodeficiency syndrome, or hepatitis.

In some embodiments, the disclosure relates to treating a viral infection by administering a TLR5 ligand, typically flagellin, in combination with a second antiviral agent. In further embodiments, the subject is co-administered with abacavir, acyclovir, acyclovir, adefovir, amantadine, amprenavir, rintatolimod (AMPLIGEN™), umifenovir (ARBIDOL™), atazanavir, efavirenz and emtricitabine and tenofovir disoproxil fumarate (ATRIPLA™), boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (TAMIFLU™), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, abacavir sulfate and lamivudine and zidovudine (TRIZIVIR™), tromantadine, emtricitabine and tenofovir disoproxil fumarate (TRUVADA™), valaciclovir (VALTREX™), valganciclovir, vicriviroc, vidarabine, viramidine zalcitabine, zanamivir (RELENZA™), and/or zidovudine. In certain embodiments, the subject is administered a pharmaceutical composition comprising TLR5 ligand, typically flagellin, and a second antiviral agent.

In certain embodiments the disclosure relates to treating a subject with a viral infection after infection by administering TLR5 ligand, typically flagellin, and immunoglobulin.

In certain embodiments, the disclosure relates to treating a viral infection by administering a TLR5 ligand, typically flagellin, and a viral vaccine or in the absence of a viral vaccine. In some embodiments, a TLR5 ligand, typically flagellin, is administered in the absence of a viral nucleic acid or viral antigen.

In certain embodiments, the flagellin has SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

In some embodiments, the disclosure relates to the use of TLR5 ligand, typically flagellin, in the production of an anti-viral medicament for the treatment of a viral infection.

In certain embodiments, the disclosure relates to a fix combination pharmaceutical composition containing a flagellin.

In certain embodiments, the disclosure relates to a vaginal microbicide comprising a flagellin.

In certain embodiments, the disclosure relates to methods of treating a subject diagnosed with a viral and bacterial infection comprising administering a TLR5 ligand in combination with an antibacterial agent. In certain embodiments, the subject is administered a pharmaceutical composition comprising a TLR5 ligand and an antibacterial agent.

DETAILED DESCRIPTION

Figure 1:
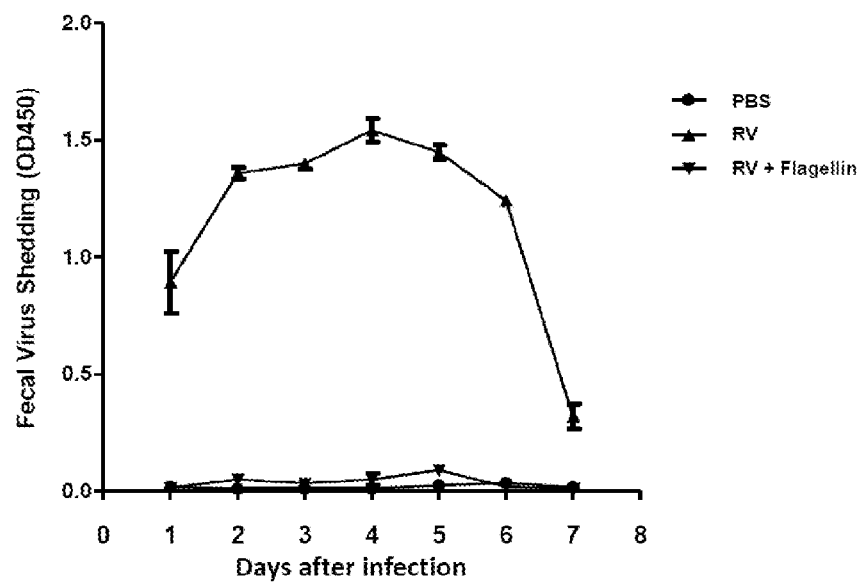
FIG. 1 shows data suggesting flagellin (FliC) protects mice from murine rotavirus (mRV) infection. C57BL/6 mice (n=5) were orally administered buffer (PBS) or a high dose of rotavirus (RV-105× minimum shedding dose) on day 0. Some mice (RV+Flagellin), received intraperitoneal injections of flagellin (20 mg/mouse) on days 0, 2, and 4. Viral infectivity is indicated by degree of viral antigens in feces, which is measured by ELISA. This experiment shows that prophylactic treatment with flagellin completely prevented infection of rotavirus.

It has been discovered that flagellin may be used to prevent and treat certain viral infections. For example flagellin cures of chronic RV infection in mice. Data herein provides that this treatment is laying (at least 150 days—permanent cure). Although for certain embodiments, it is not intended that the disclosure be limited by any particular mechanism, it is believed that flagellin utilizes TLR5, NLRC4, MyD88, IL-18, and IL-1b. Together this suggests a mechanism involving a coordinated activation of TLR5-induced transcription and inflammasome mediated processing of IL-1 and IL-18. While FliC induces PMN recruitment, its protection is fully functional in absence of neutrophils. Similar results were obtained for NK cells and macrophages. Protection is also largely independent of type I IFN. Together, these surprising results suggest a mechanism of action that is distinct for combatting viral infections.

Flagellin

As used herein, "a flagellin" refers to the monomer subunit in flagella, e.g., flagellin gene product of FliC and FljB in *S. typhimurium* and FlaA in *L. pneumophila*, or variants, analogs, homologs, derivatives, fragments or combination thereof, such as a domain or polypeptide sequence in the domain. Typically, the flagellin monomer contains D0, D1, D2, and D3 domains. An alignment of the amino acid sequences from different Gram-negative species shows a high degree of similarity in the amino and carboxy terminal domains. The central regions of these proteins may be quite divergent. It is believed that flagellin responsible for interaction with TLR5 is found in the D1 domain. Smith, K. D., et al, Nature Immunol. (2003) 4:1247-1253 disclose that TLR5 recognizes a site on the flagellin of *Salmonella typhimurium* (FliC) composed of N-terminal residues 78-129 and 135-173 and C-terminal residues 395-444. The term "a flagellin" is not intended to be limited to any particular amino acid sequence provided that it has some homology to known flagellin sequences and the molecule retains the ability to stimulate innate immune responses. The innate immune responses of flagellin are known to includes cytokine production in response to TLR (including TLR5) activation and activation of Caspase-1 and IL-1β secretion in response to certain NLRs (including Ipaf). In certain embodiments, a flagellin is contemplated to include additional amino acids within the sequence, such as in the case of fusion or chimeric proteins, provided that these proteins continue to affect an innate immune response that comprises a TLR5-mediated immune response, an Ipaf-mediated immune response or both. Also specifically contemplated are fragments, variants, analogs, homologs, or derivatives of said flagellin, and combinations thereof provided these molecules continue to affect an innate immune response that comprises a TLR5-mediated immune response, an Ipaf-mediated immune response or both. A flagellin may be isolated from natural sources, by synthetic or recombinant technologies or combinations thereof.

Individual *salmonella* serotypes usually alternate between the production of two forms of flagellin, termed phase 1 and phase 2, each specified by separate structural genes FliC and FljB. The amino acid sequences of phase-1 flagella protein of *salmonella typhimurium* (FliC) is set forth in SEQ SEQ ID NO: 1, MAQVINTNSL SLLTQNNLNK SQSALGTAIE RLSSGLRINS AKDDAAGQAI ANRFTANIKG 61 LTQASRNAND GISIAQTTEG ALNEINNNLQ RVRELAVQSA NSTNSQSDLD SIQAEITQRL 121 NEIDRVSGQT QFNGVKVLAQ DNTLTIQVGA NDGETIDIDL KQINSQTLGL DTLNVQQKYK 181 VSDTAATVTG YADTTIALDN STFKASATGL GGTDQKIDGD LKFDDTTGKY YAKVTVTGGT 241 GKDGYYEVSV DKTNGEVTLA GGATSPLTGG LPATATEDVK NVQVANADLT EAKAALTAAG 301 VTGTASVVKM SYTDNNGKTI DGGLAVKVGD DYYSATQNKD GSISINTTKY TADDGTSKTA 361 LNKLGGADGK TEVVSIGGKT YAASKAEGHN FKAQPDLAEA AATTTENPLQ KIDAALAQVD 421 TLRSDLGAVQ NRFNSAITNL GNTVNNLTSA RSRIEDSDYA TEVSNMSRAQ ILQQAGTSVL 481 AQANQVPQNV LSLLR.

The amino acid sequences of phase-2 flagella protein of *salmonella typhimurium* (FljB) is set forth in SEQ ID NO: 2, MAQVINTNSL SLLTQNNLNK SQSALGTAIE RLSSGLRINS AKDDAAGQAI ANRFTANIKG 61 LTQASRNAND GISIAQTTEG ALNEINNNLQ RVRELAVQSA NSTNSQSDLD SIQAEITQRL 121 NEIDRVSGQT QFNGVKVLAQ DNTLTIQVGA NDGETIDIDL KQINSQTLGL DSLNVQKAYD 181 VKDTAVTTKA YANNGTTLDV SGLDDAAIKA ATGGTNGTAS VTGGAVKFDA DNNKYFVTIG 241 GFTGADAAKN GDYEVNVATD GTVTLAAGAT KTTMPAGATT KTEVQELKDT PAVVSADAKN 301 ALIAGGVDAT DANGAELVKM SYTDKNGKTI EGGYALKAGD KYYAADYDEA TGAIKAKTTS 361 YTAADGTTKT AANQLGGVDG KTEVVTIDGK TYNASKAAGH DFKAQPELAE AAAKTTENPL 421 QKIDAALAQV DALRSDLGAV QNRFNSAITN LGNTVNNLSE ARSRIEDSDY ATEVSNMSRA 481 QILQQAGTSV LAQANQVPQN VLSLLR.

The amino acid sequences of F41 fragment of flagellin of *salmonella typhimurium* is set forth in SEQ ID NO: 3, FTANIKGLTQ ASRNANDGIS IAQTTEGALN EINNNLQRVR ELAVQSANST NSQSDLDSIQ 61 AEITQRLNEI DRVSGQTQFN GVKVLAQDNT LTIQVGANDG ETIDIDLKQI NSQTLGLDTL 121 NVQQKYKVSD TAATVTGYAD TTIALDNSTF KASATGLGGT DQKIDGDLKF DDTTGKYYAK 181 VTVTGGTGKD GYYEVSVDKT NGEVTLAGGA TSPLTGGLPA TATEDVKNVQ VANADLTEAK 241 AALTAAGVTG TASVVKMSYT DNNGKTIDGG LAVKVGDDYY SATQNKDGSI SINTTKYTAD 301 DGTSKTALNK LGGADGKTEV VSIGGKTYAA SKAEGHNFKA QPDLAEAAAT TTENPLQKID 361 AALAQVDTLR SDLAAVQNRF NSAITNLGNT VNNLTSAR.

The amino acid sequences of a flagellin fusion protein is set forth in SEQ ID NO:4, MALTVNTNIA SLNTQRNLNN SSASLNTSLQ RLSTGSRINS AKDDAAGLQI ANRLTSQVNG 61 LNVATKNAND GISLAQTAEG ALQQSTNILQ RMRDLSLQSA NGSNSDSERT ALNGEVKQLQ 121 KELDRISNTT TFGGRKLLDG SFGVASFQVG SAANEIISVG IGGGKLMIKL KFGVFFTVLL 181 SSAYAHGTPQ NITDLCAEYH NTQIHTLNDK IFSYTESLAG KREMAIITFK NGATFQVEVP 241 GSQHIDSQKK AIERMKDTLR IAYLTEAKVE KLCVWNNKTP HAIAAISMAN.

Polypeptide fragments of flagellin include SEQ ID NO: 5, GALNEINNNL QRVRELAVQ SANSTNSQS DLDSIQAE ITQ; SEQ ID NO: 6, TQFSGVKVLAQDNTLTIQV-GANDGET IDIDLKQINS QTLGLDTL; SEQ ID NO: 7, EGALNEINN NLQRVRELA VQSANSTNS QSDLD-SIQAEITQRLNEIDRVNG; SEQ ID NO: 8, MAQVINTNSL SLLTQNNLNK SQSALGTAI ERLSSGL-RINSAKDDAAGQAIANF TANIKGLTQA SRNANDGISI AQTTEGALN EINNNLQRVRELAVQS; SEQ ID NO: 9, LQKIDAALAQVDTLRSDLGAVQNRFNSAITNL; SEQ ID NO: 10, TLRSDLGAVQNRFNSAITNLGNTVNNLSS; and SEQ ID NO: 11, EQAAKTTEN PLQKIDAALAQVDTLRSDLGAVQNRFNSAITNLGNT-VNNLS S.

Combination of fragments of flagellin include SEQ ID NO: 12, Met Arg Gly Ser His His His His His His Gly Met Ala Ser Met Thr1 Gly Gln Gln Met Gly Arg Asp Leu Tyr Asp Asp Asp Asp Lys Asp Pro Met Ala Gln Val Ile Asn Thr Asn Ser Leu Ser Leu Leu Thr Gln Asn Asn Leu Asn Lys Ser Gln Ser Ser Leu Ser Ser Ala Ile Glu Arg Leu Ser Ser Gly Leu Arg Ile Asn Ser Ala Lys Asp Asp Ala Ala Gly Gln Ala Ile Ala Asn Arg Phe Thr Ser Asn Ile Lys Gly Leu Thr Gln Ala Ser Arg Asn Ala Asn Asp Gly Ile Ser Ile Ala Gln Thr Thr Glu Gly Ala Leu Asn Glu Ile Asn Asn Asn Leu Gln Arg Val Arg Glu Leu Ser Val Gln Ala Thr Asn Gly Thr Asn Ser Asp Ser Asp Leu Lys Ser Ile Gln Asp Glu Ile Gln Gln Arg Leu Glu Glu Ile Asp Arg Val Ser Asn Gln Thr Gln Phe Asn Gly Val Lys Val Leu Ser Gln Asp Asn Gln Met Lys Ile Gln Val Gly Ala Asn Asp Gly Thr Thr Ile Thr Ile Asp Leu Gln Lys Ile Asp Val Lys Ser Leu Gly Leu Asp Gly Phe Asn Val Asn Ser Pro Gly Ile Ser Gly Gly Gly Gly Gly Ile Leu Asp Ser Met Gly Thr Leu Ile Asn Glu Asp Ala Ala Ala Ala Lys Lys Ser Thr Ala Asn Pro Leu Ala Ser Ile Asp Ser Ala Leu Ser Lys Val Asp Ala Val Arg Ser Ser Leu Gly Ala Ile Gln Asn Arg Phe Asp Ser Ala Ile Thr Asn Leu Gly Asn Thr Val Thr Asn Leu Asn Ser Ala Arg Ser Arg Ile Glu Asp Ala Asp Tyr Ala Thr Glu Val Ser Asn Met Ser Lys Ala Gln Ile Leu Gln Gln Ala Gly Thr Ser Val Leu Ala Gln Ala Asn Gln Val Pro Gln Asn Val Leu Ser Leu Leu Arg. This protein is also known as CBLB502 (AA') as provided for in U.S. Published Patent Application No. 2009/0011982 hereby incorporated by reference. CBLB502 is currently under clinical investigation to treat Acute Radiation Syndrome (ARS).

Viruses

It has been discovered that flagellin not only prevents certain viral infections, but flagellin also cures certain chronic viral infections. In some embodiments, the disclosure relates to methods of treating a viral infection comprising administering a flagellin to a subject that is diagnosed with, suspected of, or exhibiting symptoms of a viral infection.

Viruses are infectious agents that can typically replicate inside the living cells of organisms. Virus particles (virions)

usually consist of nucleic acids, a protein coat, and in some cases an envelope of lipids that surrounds the protein coat. The shapes of viruses range from simple helical and icosahedral forms to more complex structures. Virally coded protein subunits will self-assemble to form a capsid, generally requiring the presence of the virus genome. Complex viruses code for proteins that assist in the construction of their capsid. Proteins associated with nucleic acid are known as nucleoproteins, and the association of viral capsid proteins with viral nucleic acid is called a nucleocapsid.

Viruses are transmitted by a variety of methods including direct or body fluid contact, e.g., blood, tears, semen, preseminal fluid, saliva, milk, vaginal secretions, lesions; droplet contact, fecal-oral contact, or as a result of an animal bite or birth.

A virus has either DNA or RNA genes and is called a DNA virus or a RNA virus respectively. A viral genome is either single-stranded or double-stranded. Some viruses contain a genome that is partially double-stranded and partially single-stranded. For viruses with RNA or single-stranded DNA, the strands are said to be either positive-sense (called the plus-strand) or negative-sense (called the minus-strand), depending on whether it is complementary to the viral messenger RNA (mRNA). Positive-sense viral RNA is identical to viral mRNA and thus can be immediately translated by the host cell. Negative-sense viral RNA is complementary to mRNA and thus must be converted to positive-sense RNA by an RNA polymerase before translation. DNA nomenclature is similar to RNA nomenclature, in that the coding strand for the viral mRNA is complementary to it (negative), and the non-coding strand is a copy of it (positive).

Antigenic shift, or reassortment, can result in novel strains. Viruses undergo genetic change by several mechanisms. These include a process called genetic drift where individual bases in the DNA or RNA mutate to other bases. Antigenic shift occurs when there is a major change in the genome of the virus. This can be a result of recombination or reassortment. RNA viruses often exist as quasispecies or swarms of viruses of the same species but with slightly different genome nucleoside sequences.

The genetic material within viruses, and the method by which the material is replicated, vary between different types of viruses. The genome replication of most DNA viruses takes place in the nucleus of the cell. If the cell has the appropriate receptor on its surface, these viruses enter the cell by fusion with the cell membrane or by endocytosis. Most DNA viruses are entirely dependent on the host DNA and RNA synthesizing machinery, and RNA processing machinery. Replication usually takes place in the cytoplasm. RNA viruses typically use their own RNA replicase enzymes to create copies of their genomes.

The Baltimore classification of viruses is based on the mechanism of mRNA production. Viruses must generate mRNAs from their genomes to produce proteins and replicate themselves, but different mechanisms are used to achieve this. Viral genomes may be single-stranded (ss) or double-stranded (ds), RNA or DNA, and may or may not use reverse transcriptase (RT). Additionally, ssRNA viruses may be either sense (plus) or antisense (minus). This classification places viruses into seven groups: I, dsDNA viruses (e.g. adenoviruses, herpesviruses, poxviruses); II, ssDNA viruses (plus)sense DNA (e.g. parvoviruses); III, dsRNA viruses (e.g. reoviruses); IV, (plus)ssRNA viruses (plus)sense RNA (e.g. picornaviruses, togaviruses); V, (minus)ssRNA viruses (minus)sense RNA (e.g. orthomyxoviruses, Rhabdoviruses); VI, ssRNA-RT viruses (plus)sense RNA with DNA intermediate in life-cycle (e.g. retroviruses); and VII, dsDNA-RT viruses (e.g. hepadnaviruses).

In certain embodiments, the subject is diagnosed to have a virus by nucleic acid detection or viral antigen detection.
Cytomegalovirus (CMV)

CMV belongs to the Betaherpesvirinae subfamily of Herpesviridae. In humans it is commonly known as HCMV or Human Herpesvirus 5 (HHV-5). Herpesviruses typically share a characteristic ability to remain latent within the body over long periods. HCMV infection may be life threatening for patients who are immunocompromised. In certain embodiments, the disclosure relates to methods of treating a subject diagnosed with cytomegalovirus or preventing a cytomegalovirus infection by administration of a flagellin. In certain embodiments, the subject is immunocompromised. In typical embodiments, the subject is an organ transplant recipient, undergoing hemodialysis, diagnosed with cancer, receiving an immunosuppressive drug, and/or diagnosed with an HIV-infection. In certain embodiments, the subject may be diagnosed with cytomegalovirus hepatitis, the cause of fulminant liver failure, cytomegalovirus retinitis (inflammation of the retina, may be detected by ophthalmoscopy), cytomegalovirus colitis (inflammation of the large bowel), cytomegalovirus pneumonitis, cytomegalovirus esophagitis, cytomegalovirus mononucleosis, polyradiculopathy, transverse myelitis, and subacute encephalitis. In certain embodiments, flagellin is administered in combination with an antiviral agent such as valganciclovir or ganciclovir. In certain embodiments, the subject undergoes regular serological monitoring.

HCMV infections of a pregnant subject may lead to congenital abnormalities. Congenital HCMV infection occurs when the mother suffers a primary infection (or reactivation) during pregnancy. In certain embodiments, the disclosure relates to methods of treating a pregnant subject diagnosed with cytomegalovirus or preventing a cytomegalovirus infection in a subject at risk for, attempting to become, or currently pregnant by administering a flagellin.

Subjects who have been infected with CMV typically develop antibodies to the virus. A number of laboratory tests that detect these antibodies to CMV have been developed. The virus may be cultured from specimens obtained from urine, throat swabs, bronchial lavages and tissue samples to detect active infection. One may monitor the viral load of CMV-infected subjects using PCR. CMV pp65 antigenemia test is an immunoaffinity based assay for identifying the pp65 protein of cytomegalovirus in peripheral blood leukocytes. CMV should be suspected if a patient has symptoms of infectious mononucleosis but has negative test results for mononucleosis and Epstein-Barr virus, or if they show signs of hepatitis, but have negative test results for hepatitis A, B, and C. A virus culture can be performed at any time the subject is symptomatic. Laboratory testing for antibody to CMV can be performed to determine if a subject has already had a CMV infection.

The enzyme-linked immunosorbant assay (or ELISA) is the most commonly available serologic test for measuring antibody to CMV. The result can be used to determine if acute infection, prior infection, or passively acquired maternal antibody in an infant is present. Other tests include various fluorescence assays, indirect hemagglutination, (PCR), and latex agglutination. An ELISA technique for CMV-specific IgM is available.

Hepatitis B Virus (HBV)

Hepatitis B virus is a hepadnavirus. The virus particle, (virion) consists of an outer lipid envelope and an icosahedral nucleocapsid core composed of protein. The genome of HBV is made of circular DNA, but the DNA is not fully double-stranded. One end of the strand is linked to the viral DNA polymerase. The virus replicates through an RNA intermediate form by reverse transcription. Replication typically takes place in the liver where it causes inflammation (hepatitis). The virus spreads to the blood where virus-specific proteins and their corresponding antibodies are found in infected people. Blood tests for these proteins and antibodies are used to diagnose the infection.

Hepatitis B virus gains entry into the cell by endocytosis. Because the virus multiplies via RNA made by a host enzyme, the viral genomic DNA has to be transferred to the cell nucleus by host chaperones. The partially double stranded viral DNA is then made fully double stranded and transformed into covalently closed circular DNA (cccDNA) that serves as a template for transcription of viral mRNAs. The virus is divided into four major serotypes (adr, adw, ayr, ayw) based on antigenic epitopes presented on its envelope proteins, and into eight genotypes (A-H) according to overall nucleotide sequence variation of the genome.

The hepatitis B surface antigen (HBsAg) is typically used to screen for the presence of this infection. It is the first detectable viral antigen to appear during infection. However, early in an infection, this antigen may not be present and it may be undetectable later in the infection if it is being cleared by the host. The infectious virion contains an inner "core particle" enclosing viral genome. The icosahedral core particle is made of core protein, alternatively known as hepatitis B core antigen, or HBcAg. IgM antibodies to the hepatitis B core antigen (anti-HBc IgM) may be used as a serological marker. Hepatitis B e antigen (HBeAg) may appear. The presence of HBeAg in the serum of the host is associated with high rates of viral replication. Certain variants of the hepatitis B virus do not produce the 'e' antigen, If the host is able to clear the infection, typically the HBsAg will become undetectable and will be followed by IgG antibodies to the hepatitis B surface antigen and core antigen, (anti-HBs and anti HBc IgG). The time between the removal of the HBsAg and the appearance of anti-HBs is called the window period. A person negative for HBsAg but positive for anti-HBs has either cleared an infection or has been vaccinated previously. Individuals who remain HBsAg positive for at least six months are considered to be hepatitis B carriers. Carriers of the virus may have chronic hepatitis B, which would be reflected by elevated serum alanine aminotransferase levels and inflammation of the liver which may be identified by biopsy. Nucleic acid (PCR) tests have been developed to detect and measure the amount of HBV DNA in clinical specimens.

Acute infection with hepatitis B virus is associated with acute viral hepatitis. Acute viral hepatitis typically begins with symptoms of general ill-health, loss of appetite, nausea, vomiting, body aches, mild fever, dark urine, and then progresses to development of jaundice. Chronic infection with hepatitis B virus may be either asymptomatic or may be associated with a chronic inflammation of the liver (chronic hepatitis), possibly leading to cirrhosis. Having chronic hepatitis B infection increases the incidence of hepatocellular carcinoma (liver cancer).

During HBV infection, the host immune response causes both hepatocellular damage and viral clearance. The adaptive immune response, particularly virus-specific cytotoxic T lymphocytes (CTLs), contributes to most of the liver injury associated with HBV infection. By killing infected cells and by producing antiviral cytokines capable of purging HBV from viable hepatocytes, CTLs eliminate the virus. Although liver damage is initiated and mediated by the CTLs, antigen-nonspecific inflammatory cells can worsen CTL-induced immunopathology, and platelets activated at the site of infection may facilitate the accumulation of CTLs in the liver.

Therapeutic agents can stop the virus from replicating, thus minimizing liver damage. In certain embodiments, the disclosure relates to methods of treating a subject diagnosed with HBV by administering a flagellin. In certain embodiments, the subject is immunocompromised. In certain embodiments, the flagellin is administered in combination with another antiviral agent such as lamivudine, adefovir, tenofovir, telbivudine, and entecavir, and/or immune system modulators interferon alpha-2a and pegylated interferon alpha-2a (Pegasys). In certain embodiments, the disclosure relates to preventing an HBV infection in an immunocompromised subject at risk of infection by administering a flagellin and optionally one or more antiviral agents. In certain embodiments, the subject is at risk of an infection because the sexual partner of the subject is diagnosed with HBV.

Hepatitis C Virus (HCV)

The hepatitis C virus is a single-stranded, positive sense RNA virus. It is the only known member of the hepacivirus genus in the family Flaviviridae. There are six major genotypes of the hepatitis C virus, which are indicated numerically. The hepatitis C virus particle consists of a core of genetic material (RNA), surrounded by an icosahedral protective shell, and further encased in a lipid envelope. Two viral envelope glycoproteins, E1 and E2, are embedded in the lipid envelope. The genome consists of a single open reading frame translated to produce a single protein. This large pre-protein is later cut by cellular and viral proteases into smaller proteins that allow viral replication within the host cell, or assemble into the mature viral particles, e.g., E1, E2, NS2, NS3, NS4, NS4A, NS4B, NS5, NS5A, and NS5B.

HCV leads to inflammation of the liver, and chronic infection leads to cirrhosis. Most people with hepatitis C infection have the chronic form. Diagnosis of HCV can occur via nucleic acid analysis of the 5'-noncoding region. ELISA assay may be performed to detect hepatitis C antibodies and RNA assays to determine viral load. Subjects infected with HCV may exhibit symptoms of abdominal pain, ascites, dark urine, fatigue, generalized itching, jaundice, fever, nausea, pale or clay-colored stools and vomiting.

Therapeutic agents in some cases may suppress the virus for a long period of time. Typical medications are a combination of interferon alpha and ribavirin. Subjects may receive injections of pegylated interferon alpha. Genotypes 1 and 4 are less responsive to interferon-based treatment than are the other genotypes (2, 3, 5 and 6). In certain embodiments, the disclosure relates to treating a subject with HCV by administering a flagellin to a subject exhibiting symptoms or diagnosed with HCV. In certain embodiments, flagellin is administered in combination with interferon alpha and another antiviral agent such as ribavirin, and/or a protease inhibitor such as telaprevir or boceprevir. In certain embodiments, the subject is diagnosed with genotype 2, 3, 5, or 6. In other embodiments, the subject is diagnosed with genotype 1 or 4.

Human Immunodeficiency Virus (HIV)

HIV is a lentivirus (a member of the retrovirus family) that causes acquired immunodeficiency syndrome (AIDS). Lentiviruses are transmitted as single-stranded, positive-sense, enveloped RNA viruses. Upon entry of the target cell, the viral RNA genome is converted to double-stranded DNA by a virally encoded reverse transcriptase. This viral DNA is then integrated into the cellular DNA by a virally encoded integrase, along with host cellular co-factors. There are two species of HIV. HIV-1 is sometimes termed LAV or HTLV-III.

HIV infects primarily vital cells in the human immune system such as helper T cells (CD4+ T cells), macrophages, and dendritic cells. HIV infection leads to low levels of CD4+ T cells. When CD4+ T cell numbers decline below a critical level, cell-mediated immunity is lost, and the body becomes progressively more susceptible to other viral or bacterial infections. Subjects with HIV typically develop malignancies associated with the progressive failure of the immune system.

The viral envelope is composed of two layers of phospholipids taken from the membrane of a human cell when a newly formed virus particle buds from the cell. Embedded in the viral envelope are proteins from the host cell and a HIV protein known as Env. Env contains glycoproteins gp120, and gp41. The RNA genome consists of at structural landmarks (LTR, TAR, RRE, PE, SLIP, CRS, and INS) and nine genes (gag, pol, and env, tat, rev, nef, vif, vpr, vpu, and sometimes a tenth tev, which is a fusion of tat env and rev) encoding 19 proteins. Three of these genes, gag, pol, and env, contain information needed to make the structural proteins for new virus particles. HIV-1 diagnosis is typically done with antibodies in an ELISA, Western blot, or immunoaffinity assays or by nucleic acid testing (e.g., viral RNA or DNA amplification).

HIV is typically treated with a combination of antiviral agent, e.g., two nucleoside-analogue reverse transcription inhibitors and one non-nucleoside-analogue reverse transcription inhibitor or protease inhibitor. The three drug combination is commonly known as a triple cocktail. In certain embodiments, the disclosure relates to treating a subject diagnosed with HIV by administering flagellin in combination with two nucleoside-analogue reverse transcription inhibitors and one non-nucleoside-analogue reverse transcription inhibitor or protease inhibitor.

In certain embodiments, the disclosure relates to treating a subject by administering flagellin, emtricitabine, tenofovir, and efavirenz. In certain embodiments, the disclosure relates to treating a subject by administering flagellin, emtricitabine, tenofovir and raltegravir. In certain embodiments, the disclosure relates to treating a subject by administering flagellin, emtricitabine, tenofovir, ritonavir and darunavir. In certain embodiments, the disclosure relates to treating a subject by administering flagellin, emtricitabine, tenofovir, ritonavir and atazanavir.

Banana lectin (BanLec or BanLec-1) is one of the predominant proteins in the pulp of ripe bananas and has binding specificity for mannose and mannose-containing oligosaccharides. BanLec binds to the HIV-1 envelope protein gp120. In certain embodiments, the disclosure relates to treating viral infections, such as HIV, by administering a flagellin in combination with a banana lectin.

Combination Therapies

In some embodiments, the disclosure relates to treating a viral infection by administering a flagellin in combination with a second antiviral agent. In further embodiments, flagellin is administered in combination with one or more of the following agents: abacavir, acyclovir, acyclovir, adefovir, amantadine, amprenavir, rintatolimod (AMPLIGEN™), umifenovir (ARBIDOL™), atazanavir, efavirenz and emtricitabine and tenofovir disoproxil fumarate (ATRIPLA™), boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (TAMIFLU™), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, abacavir sulfate and lamivudine and zidovudine (TRIZIVIR™), tromantadine, emtricitabine and tenofovir disoproxil fumarate (TRUVADA™), valaciclovir (VALTREX™), valganciclovir, vicriviroc, vidarabine, viramidine zalcitabine, zanamivir (RELENZA™), and/or zidovudine (AZT).

Antiviral agents include, but are not limited to, protease inhibitors (PIs), integrase inhibitors, entry inhibitors (fusion inhibitors), maturation inhibitors, and reverse transcriptase inhibitors (anti-retrovirals). Combinations of antiviral agents create multiple obstacles to viral replication, i.e., to keep the number of offspring low and reduce the possibility of a superior mutation. If a mutation that conveys resistance to one of the agents being taken arises, the other agents continue to suppress reproduction of that mutation. For example, a single anti-retroviral agent has not been demonstrated to suppress an HIV infection for long. These agents are typically taken in combinations in order to have a lasting effect. As a result, the standard of care is to use combinations of anti-retrovirals.

Reverse transcribing viruses replicate using reverse transcription, i.e., the formation of DNA from an RNA template. Retroviruses often integrate the DNA produced by reverse transcription into the host genome. They are susceptible to antiviral drugs that inhibit the reverse transcriptase enzyme. In certain embodiments the disclosure relates to methods of treating viral infections by administering a TLR5 ligand, such as flagellin, and a retroviral agent such as nucleoside and nucleotide reverse transcriptase inhibitors (NRTI) and/or a non-nucleoside reverse transcriptase inhibitors (NNRTI). Examples of nucleoside reverse transcriptase inhibitors include zidovudine, didanosine, zalcitabine, stavudine, lamivudine, abacavir, emtricitabine, entecavir, apricitabine. Examples of nucleotide reverse transcriptase inhibitors include tenofovir and adefovir. Examples of non-nucleoside reverse transcriptase inhibitors include efavirenz, nevirapine, delavirdine, and etravirine.

In certain embodiments, the disclosure relates to methods of treating a viral infection by administering a flagellin in combination with an antiviral drug, e.g., 2',3'-dideoxyinosine and a cytostatic agent, e.g., hydroxyurea.

Human immunoglobulin G (IgG) antibodies are believed to have opsonizing and neutralizing effects against certain viruses. IgG is sometimes administered to a subject diagnosed with immune thrombocytopenic purpura (ITP) secondary to a viral infection since certain viruses such as, HIV and hepatitis, cause ITP. In certain embodiments, the disclosure relates to methods of treating or preventing viral infections comprising administering a flagellin in combination with an immunoglobulin to a subject. IgG is typically manufactured from large pools of human plasma that are screened to reduce the risk of undesired virus transmission. The Fc and Fab functions of the IgG molecule are usually retained. Therapeutic IgGs include PRIVIGEN™, HIZENTRA™, and WINRHO™. WINRHO™ is an immunoglobulin (IgG) fraction containing antibodies to the Rho(D) antigen (D antigen). The antibodies have been shown to increase platelet counts in Rho(D) positive subjects with ITP. The mechanism is thought to be due to the formation of anti- Rho(D) (anti-D)-coated RBC complexes resulting in Fc receptor blockade, thus sparing antibody-coated platelets.

In some embodiments, the disclosure relates to treating a viral infection arising as a complication of a bacterial infection by administering a flagellin in combination with an antibiotic drug. In further embodiments, the subject is co-administered with an antibiotic selected from the group comprising of Sulfonamides, Diaminopyrimidines, Quinolones, Beta-lactam antibiotics, Cephalosporins, Tetracyclines, Notribenzene derivatives, Aminoglycosides, Macrolide antibiotics, Polypeptide antibiotics, Nitrofuran derivatives, Nitroimidazoles, Nicotinin acid derivatives, Polyene antibiotics, Imidazole derivatives or Glycopeptide, Cyclic lipopeptides, Glycylcyclines and Oxazolidinones. In further embodiments, these antibiotics include but are not limited to Sulphadiazine, Sulfones—[Dapsone (DDS) and Paraaminosalicyclic (PAS)], Sulfanilamide, Sulfamethizole, Sulfamethoxazole, Sulfapyridine, Trimethoprim, Pyrimethamine, Nalidixic acids, Norfloxacin, Ciproflaxin, Cinoxacin, Enoxacin, Gatifloxacin, Gemifloxacin, Grepafloxacin, Levofloxacin, Lomefloxacin, Moxifloxacin, Ofloxacin, Pefloxacin, Sparfloxacin, Trovafloxacin, Penicillins (Amoxicillin, Ampicillin, Azlocillin, Carbenicillin, Cloxacillin, Dicloxacillin, Flucloxacillin, Hetacillin, Oxacillin, Mezlocillin, Penicillin G, Penicillin V, Piperacillin), Cephalosporins (Cefacetrile, Cefadroxil, Cefalexin, Cefaloglycin, Cefalonium, Cefaloridin, Cefalotin, Cefapirin, Cefatrizine, Cefazaflur, Cefazedone, Cefazolin, Cefradine, Cefroxadine, Ceftezole, Cefaclor, Cefonicid, Ceforanide, Cefprozil, Cefuroxime, Cefuzonam, Cefinetazole, Cefoteta, Cefoxitin, Cefcapene, Cefdaloxime, Cefdinir, Cefditoren, Cefetamet, Cefixime, Cefinenoxime, Cefodizime, Cefoperazone, Cefotaxime, Cefotiam, Cefpimizole, Cefpiramide, Cefpodoxime, Cefteram, Ceftibuten, Ceftiofur, Ceftiolen, Ceftizoxime, Ceftriaxone, Cefoperazone, Ceftazidime, Cefepime), Moxolactam, Carbapenems (Imipenem, Ertapenem, Meropenem) Monobactams (Aztreonam) Oxytetracycline, Chlortetracycline, Clomocycline, Demeclocycline, Tetracycline, Doxycycline, Lymecycline, Meclocycline, Methacycline, Minocycline, Rolitetracycline, Chloramphenicol, Amikacin, Gentamicin, Framycetin, Kanamycin, Neomicin, Neomycin, Netilmicin, Streptomycin, Tobramycin, Azithromycin, Clarithromycin, Dirithromycin, Erythromycin, Roxithromycin, Telithromycin, Polymyxin-B, Colistin, Bacitracin, Tyrothricin Notrifurantoin, Furazolidone, Metronidazole, Tinidazole, Isoniazid, Pyrazinamide, Ethionamide, Nystatin, Amphotericin-B, Hamycin, Miconazole, Clotrimazole, Ketoconazole, Fluconazole, Rifampacin, Lincomycin, Clindamycin, Spectinomycin, Chloramphenicol, Clindamycin, Colistin, Fosfomycin, Loracarbef, Metronidazole, Nitrofurantoin, Polymyxin B, Polymyxin B Sulfate, Procain, Spectinomycin, Tinidazole, Trimethoprim, Ramoplanin, Teicoplanin, Vancomycin, Trimethoprim, Sulfamethoxazole, and/or Nitrofurantoin.

Formulations

Generally, for pharmaceutical use, the compositions may be formulated as a pharmaceutical preparation comprising at least one flagellin and at least one pharmaceutically acceptable carrier, diluent or excipient and/or adjuvant, and optionally one or more further pharmaceutically active compositions.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one flagellin of the disclosure, e.g. about 10, 25, 50, 100, 200, 300 or 400 mg per unit dosage.

The compositions can be administered by a variety of routes including the oral, ocular, rectal, transdermal, subcutaneous, intravenous, intramuscular or intranasal routes, depending mainly on the specific preparation used. The composition will generally be administered in an "effective amount", by which is meant any amount of a composition that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

For an oral administration form, the composition can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compositions of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compositions, if desired with the substances customary therefore such as solubilizers, emulsifiers or further auxiliaries are brought into solution, suspension, or emulsion. The compositions can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compositions with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxy groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (pegylation) to increase the in vivo half-life of circulating therapeutic proteins.

Terms

As used herein, the term "derivative", when used in the context of a peptide or polypeptide, means a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the disclosure. Other derivatives include, but are not limited to, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

As used herein, the term "variant", when used in the context of a peptide or polypeptide, means a peptide or polypeptide that differs in amino acid sequence by the insertion, deletion, or conservative substitution of amino acids, but retain at least one biological activity. For purposes of this disclosure, "biological activity" includes, but is not limited to, the ability to be bound by a specific antibody. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. The hydropathic index of an amino acid is based on a consideration of its hydrophobicity and charge. It is known in the art that amino acids of similar hydropathic indexes can be substituted and still retain protein function. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. See, e.g., U.S. Pat. No. 4,554,101. Substitution of amino acids having similar hydrophilicity values can result in peptides retaining biological activity, for example immunogenicity, as is understood in the art. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

The terms "treatment" or "treating" include any desirable effect on the symptoms or pathology of a disease or condition, and may include even minimal reductions in one or more measurable markers of the disease or condition being treated. "Treatment" does not necessarily indicate complete eradication or cure of the disease or condition, or associated symptoms thereof. The subject receiving this treatment is any animal in need, including primates, in particular humans, and other mammals such as equines, cattle, swine and sheep; and poultry and pets in general.

In certain embodiments, the subject has a compromised or suppressed immune system. Immunosuppression reduces the activation or efficacy of the immune system. Deliberately induced immunosuppression is typically done to prevent the body from rejecting an organ transplant (e.g., bone marrow, heart, kidney, liver), treating graft-versus-host disease after a bone marrow transplant, or for the treatment of auto-immune diseases (e.g., rheumatoid arthritis, multiple sclerosis, myasthenia gravis, systemic lupus erythematosus, Crohn's disease, pemphigus, and ulcerative colitis). Immunosuppression may be accomplished by certain agents (immunosuppressants) such as, but not limited to, dactinomycin, azathioprine, mycophenolic acid, leflunomide, teriflunomide, methotrexate, tacrolimus, ciclosporin, pimecrolimus, abetimus, gusperimus, lenalidomide, anakinra, sirolimus, deforolimus, everolimus, temsirolimus, zotarolimusm, biolimus A9, T-cell receptor directed antibodies (e.g., muromonab), and IL-2 receptor directed antibodies (e.g., basiliximab and daclizumab). Since certain immunosuppressants act non-selectively, the immune system is less able to eliminate viral infections. Surgery (splenectomy), plasmapharesis, or radiation may also cause a suppressed immune system. A person who is undergoing immunosuppressant therapy, or whose immune system is weak for other reasons (for example, chemotherapy, HIV, and Lupus) is said to be immunocompromised. Neonates are considered to immunocompromised. Certain viruses such as HIV will comprise the host immune system. In certain embodiments, the disclosure relates to treating or preventing a viral infection by administering flagellin to an immunocompromised subject.

As used herein, the term "combination with" when used to describe administration of TLR5 ligand and an additional treatment means that the agent may be administered prior to, together with, or after the additional treatment, or a combination thereof.

EXPERIMENTAL

Example 1: Flagellin Protects Mice from Murine Rotavirus (EC) Infection

C57BL/6 mice (n=5) were orally administered buffer (PBS) or a high dose of rotavirus (RV-105×minimum shedding dose) on day 0. Some mice (RV+Flagellin), received intraperitoneal injections of flagellin (20 µg/mouse) on days 0, 2, and 4. In FIG. 1, viral infectivity is indicated by degree of viral antigens in feces, which is measured by ELISA. This experiment shows that prophylactic treatment with flagellin completely prevented infection of rotavirus.

Figure 2:
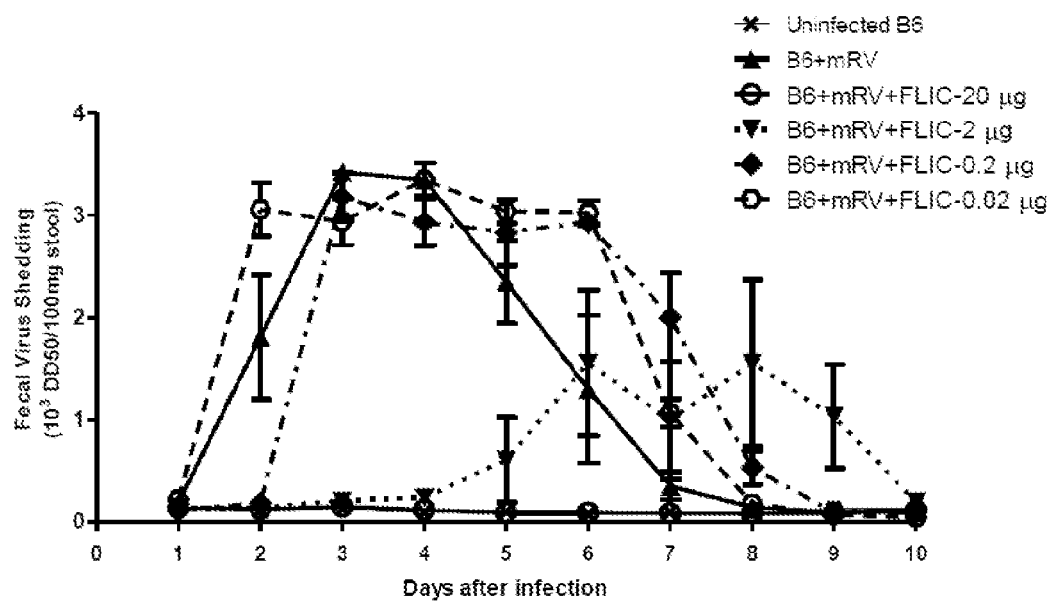
FIG. 2 shows data suggesting that flagellin (FliC) protection of mice from mRV infection is concentration-dependent. C57BL/6 mice (n=5) were orally administered buffer (PBS) or a high dose of rotavirus (RV-$10^5$× minimum shedding dose) on day 0. Some mice (RV+Flagellin), received intraperitoneal injections of flagellin (0.02-20 20 mg/mouse as indicated) on days 0, 2, 4, and 6. Viral infectivity is indicated by degree of viral antigens in feces, which is measured by ELISA. This experiment shows that treatment with 2 mg of flagellin partially prevented infection of rotavirus while 20 mg afforded complete protection.

Example 2: Concentration Dependence of Flagellin Protection Against Murine Rotavirus (EC) Infection C57BL/6 mice (n=5) were orally administered buffer (PBS) or a high dose of rotavirus (RV-105×minimum shedding dose) on day 0. Some mice (RV+Flagellin), received intraperitoneal injections of flagellin (0.02-20, 20 µg/mouse as indicated) on days 0, 2, 4, and 6. In FIG. 2, viral infectivity is indicated by degree of viral antigens in feces, which is measured by ELISA. This experiment shows that treatment with 2 µg of flagellin partially prevented infection of rotavirus while 20 µg afforded complete protection.

Figure 3:
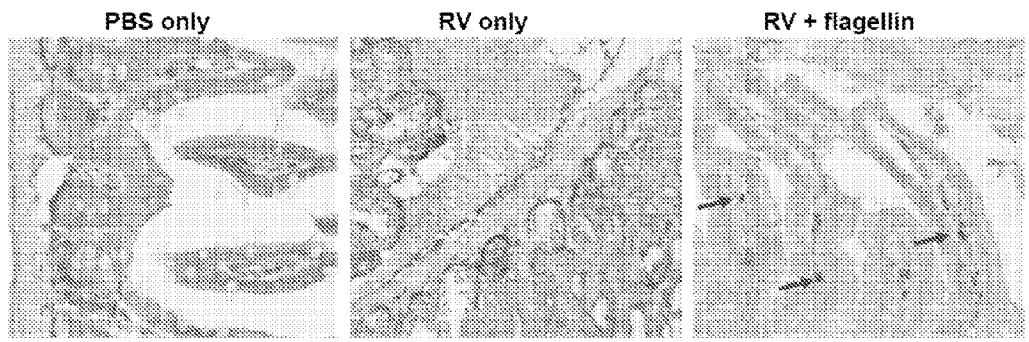
FIG. 3 shows visualization of flagellin protection against RV infection via immunohistochemical microscopy. C57BL/6 mice were orally administered buffer (PBS) or a high dose of rotavirus (RV-105× minimum shedding dose) on day 0. Some mice (RV+Flagellin), received intraperitoneal injections of flagellin (20 µg/mouse) on days 0 and 2. Mice were euthanized on day 4 and viral infectivity assessed via using ant antibody to reveal location of the viral structural components (antigens). This experiment shows that prophylactic treatment with flagellin completely prevented infection of rotavirus. The arrows in the specimen derived from the RV+Flagellin treated mouse point to phagocytic cells filled with viral antigens. These cells may mediate the protective effect of flagellin against the virus.

Example 3: Visualization of Flagellin Protection Against RV Infection Via Immunohistochemical Microscopy C57BL/6 mice were orally administered buffer (PBS) or a high dose of rotavirus (RV-105× minimum shedding dose) on day 0. Some mice (RV+Flagellin), received intraperitoneal injections of flagellin (20 µg/mouse) on days 0 and 2. Mice were euthanized on day 4 and viral infectivity assessed via using ant antibody to reveal location of the viral structural components (antigens). This experiment shows that prophylactic treatment with flagellin completely prevented infection of rotavirus. In FIG. 3, the arrows in the specimen derived from the RV+Flagellin treated mouse point to phagocytic cells filled with viral antigens. These cells may mediate the protective effect of flagellin against the virus.

Figure 4A:
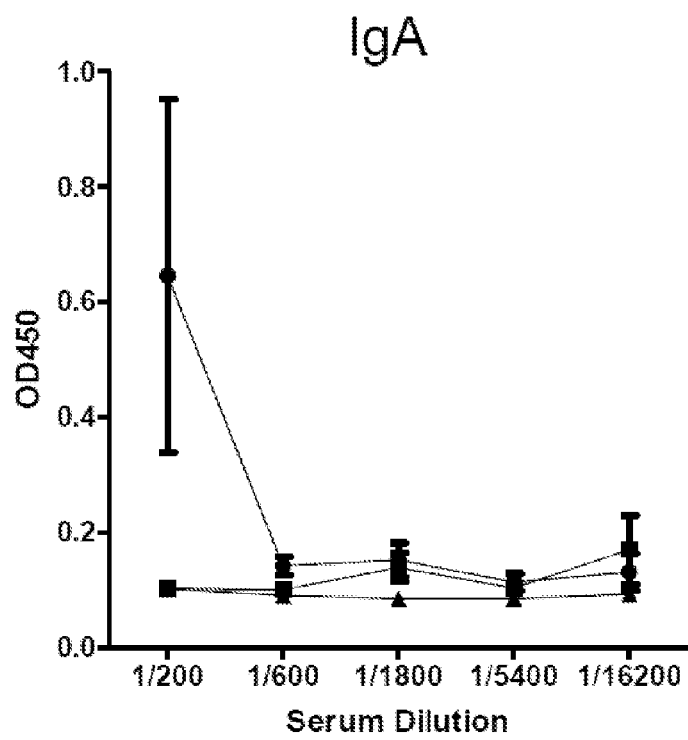
FIGS. 4A and 4B shows immunologic evidence suggesting that flagellin protects against rotavirus infection throughout the mouse. C57BL/6 mice (n=5) were orally administered buffer (PBS) or a high dose of rotavirus (RV-105× minimum shedding dose) on day 0. Some mice (RV+Flagellin), received intraperitoneal injections of flagellin (20 mg/mouse) on days 0, 2, 4, 6 and 8. Mice were bled on day 21 and levels of anti-RV antibodies (IgA and IgG) were measured by ELISA. Viral infectivity is indicated by degree of viral antigens in feces, which is measured by ELISA. These antibodies reflect the degree to which the entire mouse has been exposed to virus. That flagellin eliminates the induction of these antibodies indicates that infectivity is diminished throughout the mouse as opposed to only the intestine.
Figure 4B:
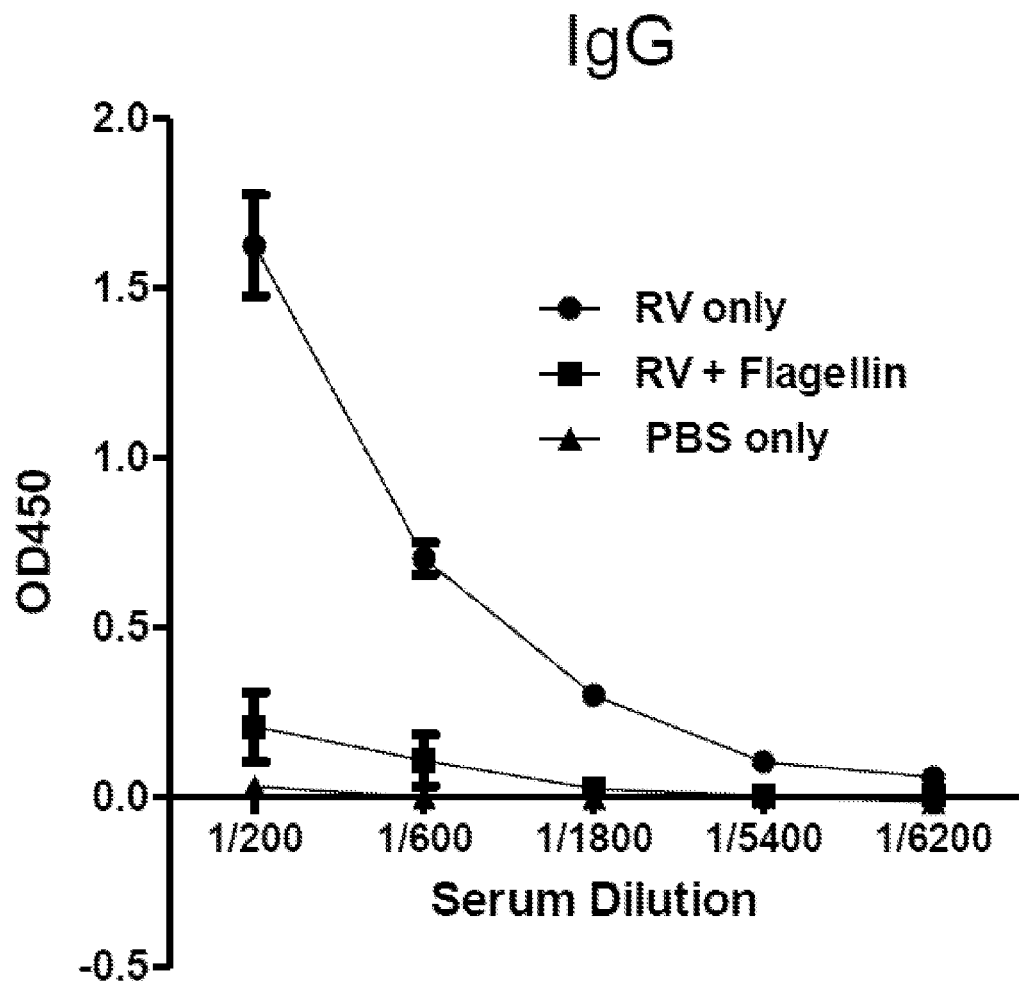

Example 4: Immunologic Evidence that Flagellin Protects Against Rotavirus Infection Throughout the Mouse C57BL/6 mice (n=5) were orally administered buffer (PBS) or a high dose of rotavirus (RV-$10^5$× minimum shedding dose) on day 0. Some mice (RV+Flagellin), received intraperitoneal injections of flagellin (20 mg/mouse) on days 0, 2, 4, 6, and 8. Mice were bled on day 21 and levels of anti-RV antibodies (IgA and IgG) were measured by ELISA. See FIGS. 4A and 4B. Viral infectivity is indicated by degree of viral antigens in feces, which is measured by ELISA. These antibodies reflect the degree to which the entire mouse has been exposed to virus. That flagellin eliminates the induction of these antibodies indicates that infectivity is diminished throughout the mouse as opposed to only the intestine.

Figure 5:
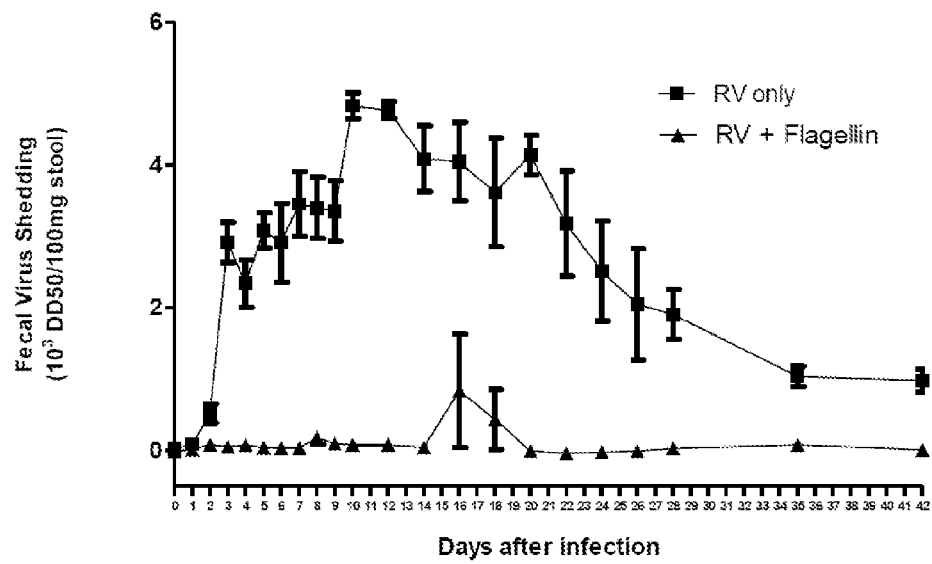
FIG. 5 shows data suggesting Flagellin protection against RV infection does not involve lymphocytes, which mediate adaptive immunity. Rag-1-deficient mice (n=5), 8 weeks of age, which lack all T and B lymphocytes, were orally administered buffer a high dose of rotavirus (RV–$10^5$× minimum shedding dose) on day 0. Some mice (RV+Flagellin), received intraperitoneal injections of flagellin (20 mg/mouse) every other day from day 0 to 20. Viral infectivity is indicated by degree of viral antigens in feces, which is measured by ELISA. This experiment shows that prophylactic treatment with flagellin completely prevented infection of rotavirus. Thus, the protective effect of flagellin against this virus is completely different than a typical vaccine and is a completely different approach than that of using flagellin as a vaccine adjuvant.

Example 5: Flagellin Protection Against RV Infection does not Involve Lymphocytes Rag-1-deficient mice (n=5), 8 weeks of age, which lack all T and B lymphocytes, which mediate adaptive immunity, were orally administered buffer a high dose of rotavirus (RV-105× minimum shedding dose) on day 0. Some mice (RV+Flagellin), received intraperitoneal injections of flagellin (20 mg/mouse) every other day from day 0 to 20. In FIG. 5, viral infectivity is indicated by degree of viral antigens in feces, which is measured by ELISA. This experiment shows that prophylactic treatment with flagellin completely prevented infection of rotavirus. Thus, the protective effect of flagellin against this virus is completely different than a typical vaccine and is a completely different approach than that of using flagellin as a vaccine adjuvant.

Example 6: Flagellin Treatment Cures Chronic Murine Rotavirus Infection

Figure 6:
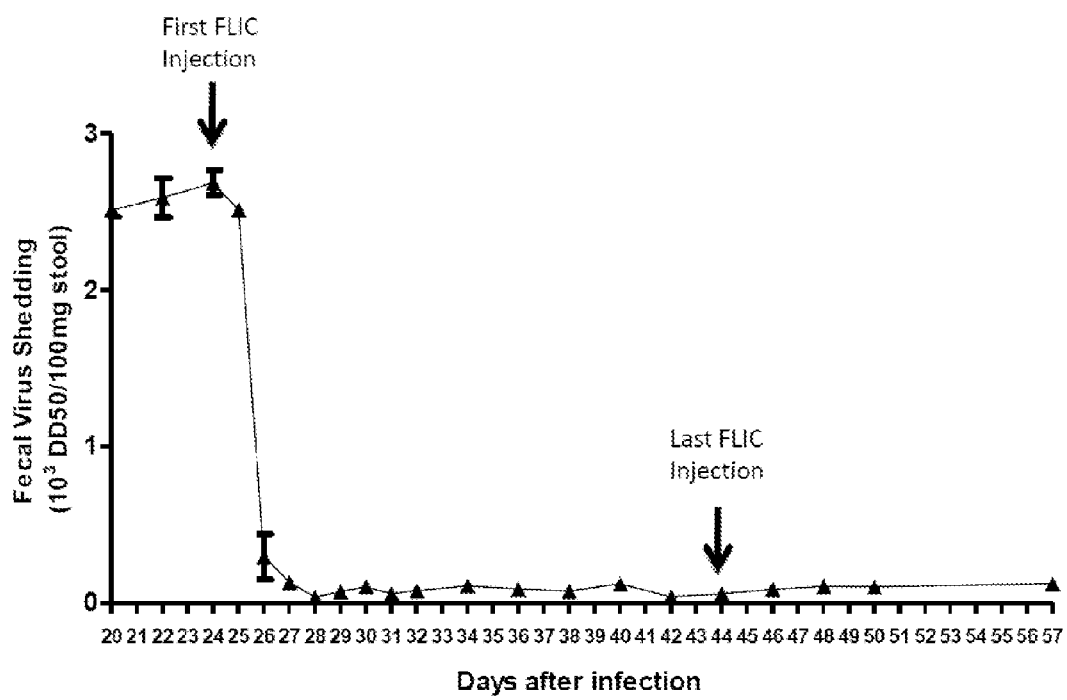
FIG. 6 shows data suggesting flagellin treatment cures chronic murine Rotavius infection. Rag-1-deficient mice (n=5), 4 weeks of age, which lack all T and B lymphocytes, were orally administered buffer a high dose of rotavirus (RV–105× minimum shedding dose) on day 0. 24 days later, at which point a chronic infection had been established, mice were received intraperitoneal injections of flagellin (20 mg/mouse) every other day from day 24 to 44 as indicated by arrows. Viral infectivity is indicated by degree of viral antigens in feces, which is measured by ELISA. This experiment shows that flagellin treatment could completely cure a chronic viral infection even in mice that are severely immunocompromised.

Rag-1-deficient mice (n=5), 4 weeks of age, which lack all T and B lymphocytes, were orally administered buffer a high dose of rotavirus (RV-105× minimum shedding dose) on day 0. 24 days later, at which point a chronic infection had been established, mice were received intraperitoneal injections of flagellin (20 mg/mouse) every other day from day 24 to 44 as indicated by arrows. In FIG. 6, viral infectivity is indicated by degree of viral antigens in feces, which is measured by ELISA. This experiment shows that flagellin treatment could completely cure a chronic viral infection even in mice that are severely immunocompromised.

Example 7: Comparing Flagellin to Lipopolysaccharide

Figure 7:
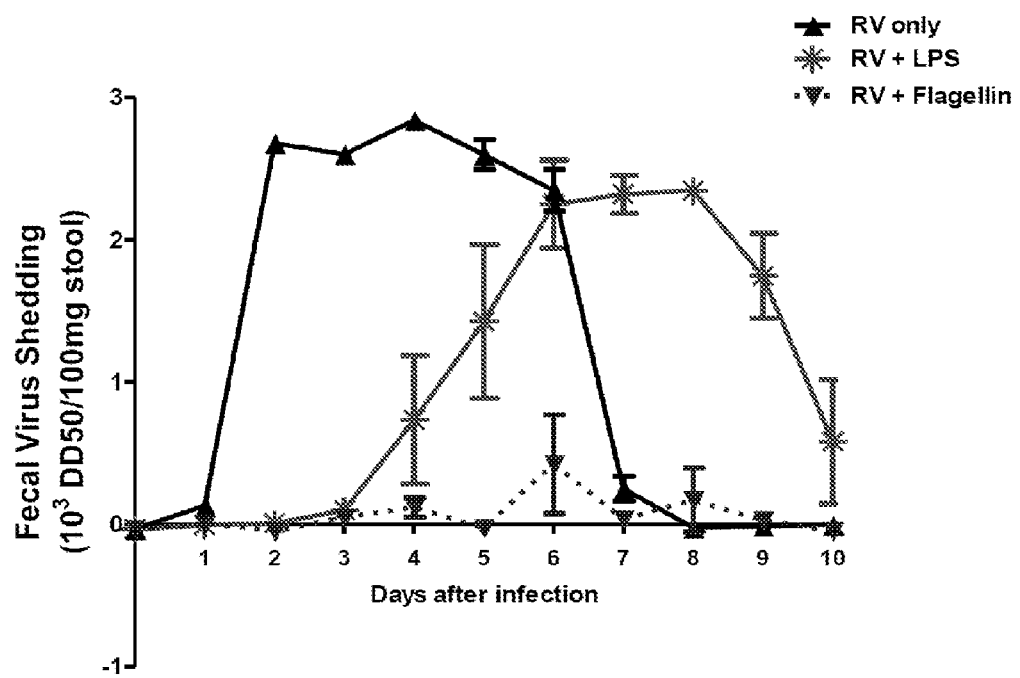
FIG. 7 shows data comparing flagellin to LPS treatments. C57BL/6 mice (n=5) were orally administered a high dose of rotavirus (RV–$10^5$× minimum shedding dose) on day 0. Some mice received intraperitoneal injections of flagellin (20 mg/mouse) or LPS (20 mg/mouse) on days 0, 2, and 4. Viral infectivity is indicated by degree of viral antigens in feces, which is measured by ELISA. This experiment shows that prophylactic treatment with flagellin completely prevented infection of rotavirus. In contrast, treatment with LPS only delayed the course of infection by a few days. Thus, the protective activity of flagellin against RV is unique to this product and is not shared by other activators of innate immunity.

C57BL/6 mice (n=5) were orally administered a high dose of rotavirus (RV-105× minimum shedding dose) on day 0. Some mice received intraperitoneal injections of flagellin (20 μg/mouse) or LPS (20 μg/mouse) on days 0, 2, and 4. In FIG. 7, viral infectivity is indicated by degree of viral antigens in feces, which is measured by ELISA. This experiment shows that prophylactic treatment with flagellin completely prevented infection of rotavirus. In contrast, treatment with LPS only delayed the course of infection by a few days. Thus, the protective activity of flagellin against RV is unique to this product and is not shared by other activators of innate immunity.

Example 8: Flagellin Protection Against RV is Mediated by TLR5

Figure 8:
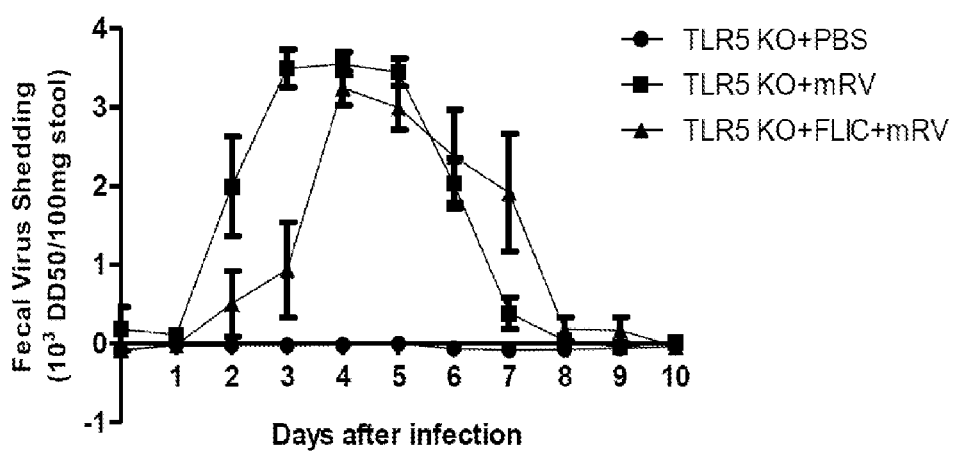
FIG. 8 shows data when administering flagellin (FliC) to TLR5 KO mice. TLR5-deficient mice (n=5) were orally administered buffer (PBS) or a high dose of rotavirus (RV–$10^5$× minimum shedding dose) on day 0. Some mice (RV+Flagellin), received intraperitoneal injections of flagellin (20 mg/mouse) on days 0, 2, and 4. Viral infectivity is indicated by degree of viral antigens in feces, which is measured by ELISA. This experiment shows that, in TLR5-deficient mice, prophylactic treatment with flagellin did not protect mice from RV infection but merely delayed the course of infection by a few days.
Figure 9:
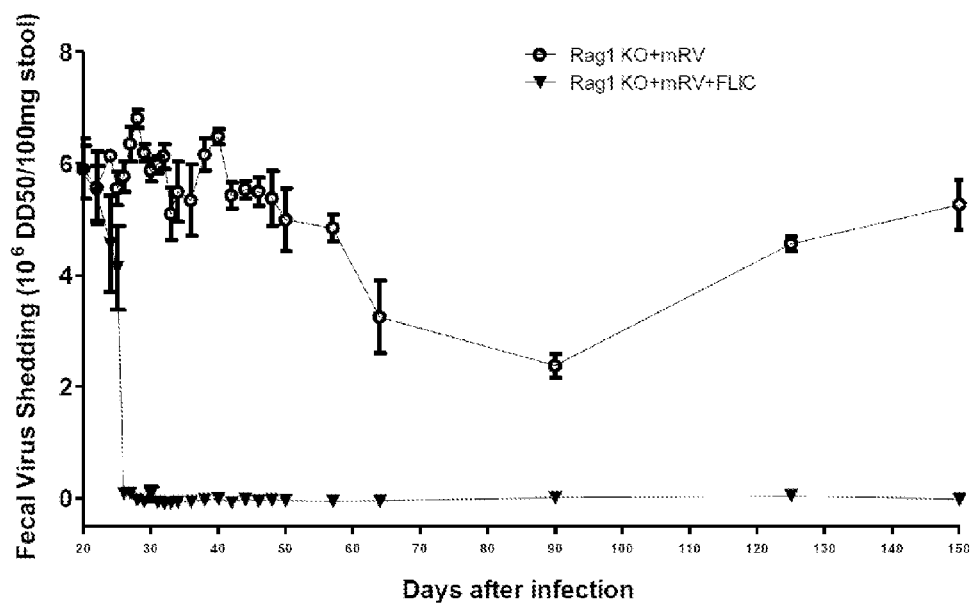
FIG. 9 shows data suggesting flagellin (FliC) demonstrates lasting cure by the flagellin treatment.
Figure 10:
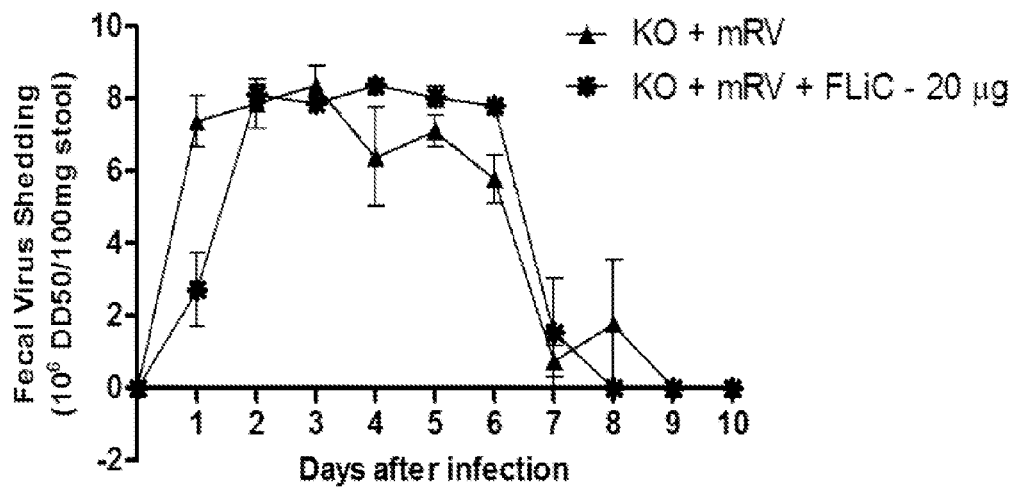
FIG. 10 shows data suggesting MyD88 is involved in flagellin meditated protection from murine Rotavirus (mRV) infection.
Figure 11A:
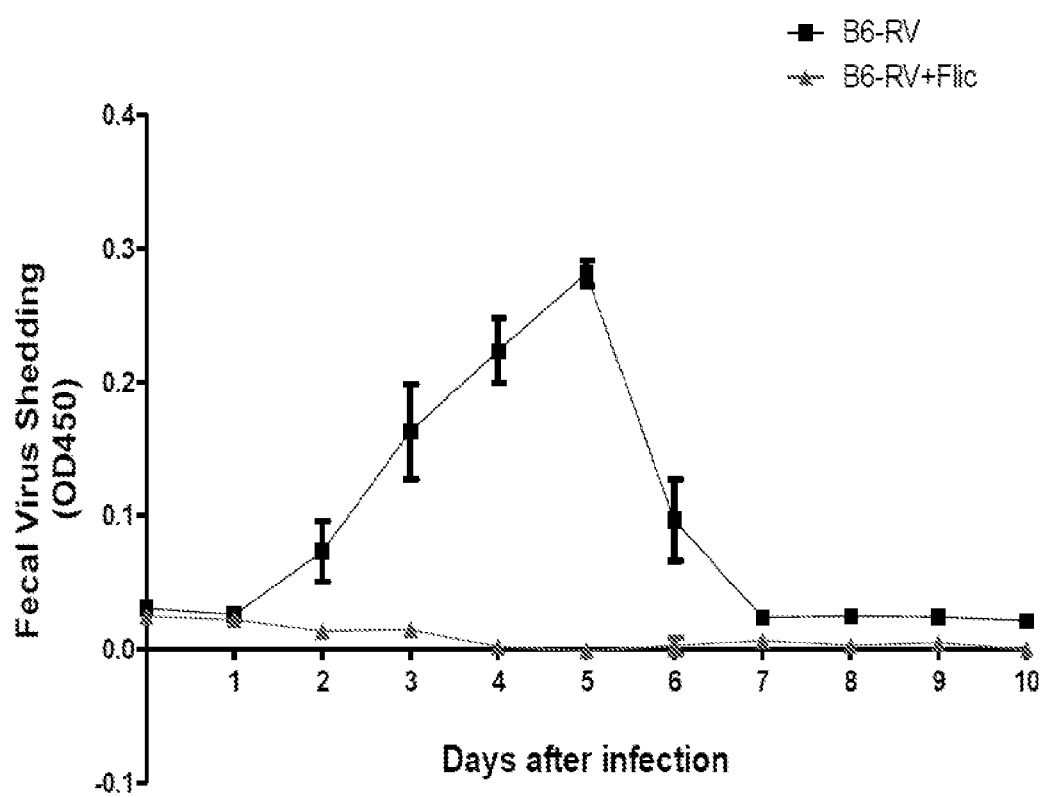
FIGS. 11A and 11B show data suggesting NLRC4 is involved in flagellin-mediated protection from mRV infection.
Figure 11B:
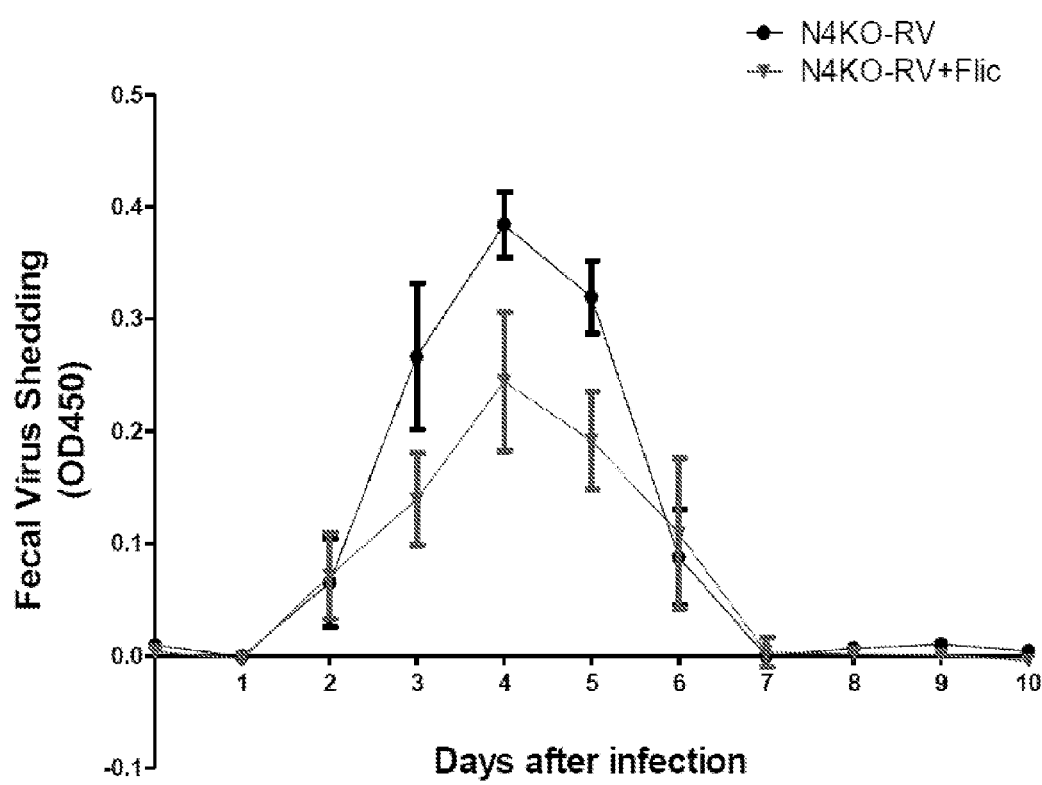
Figure 12A:
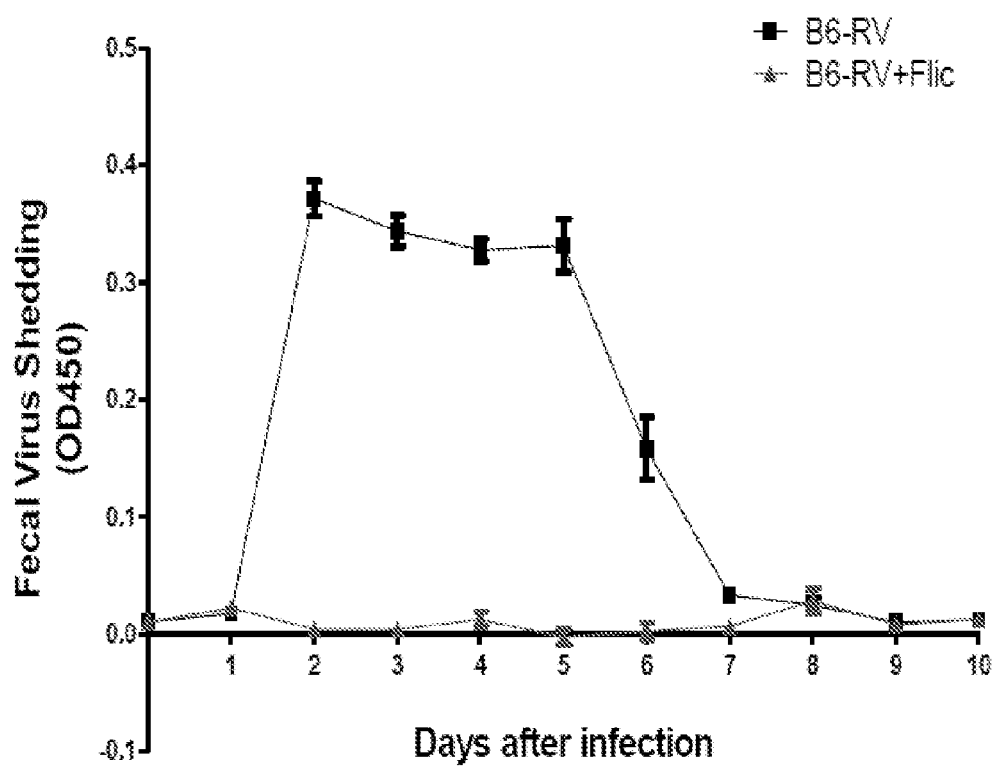
FIGS. 12A and 12B show data suggesting that IL-18 is involved in flagellin protection because flagellin protection against mRV is reduced when IL-18 is blocked.
Figure 12B:
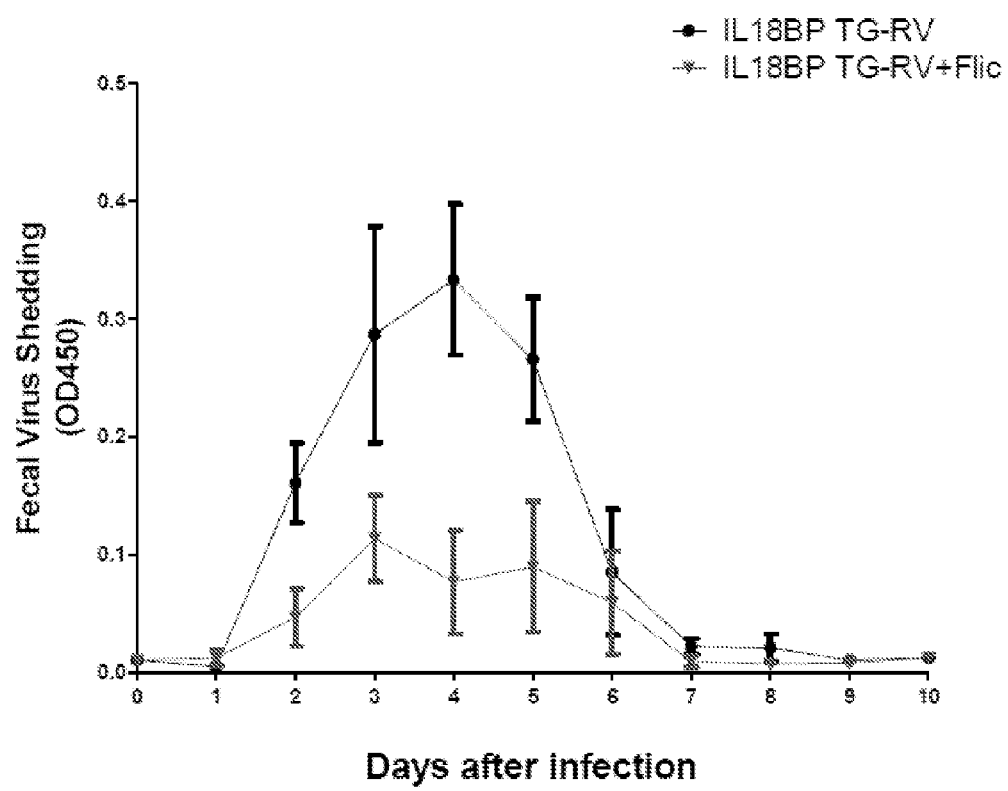
Figure 13A:
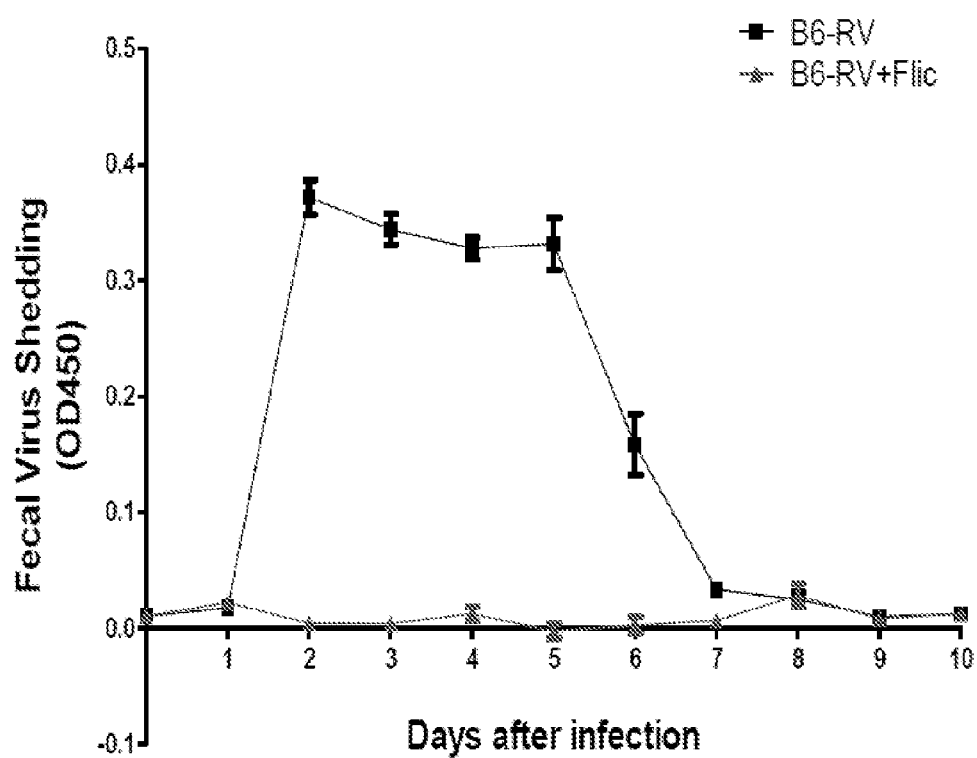
FIGS. 13A and 13B shows data suggesting the IL-1 is involved in flagellin protection because flagellin protection against mRV is reduced in the absence of functional IL-1 receptors.
Figure 13B:
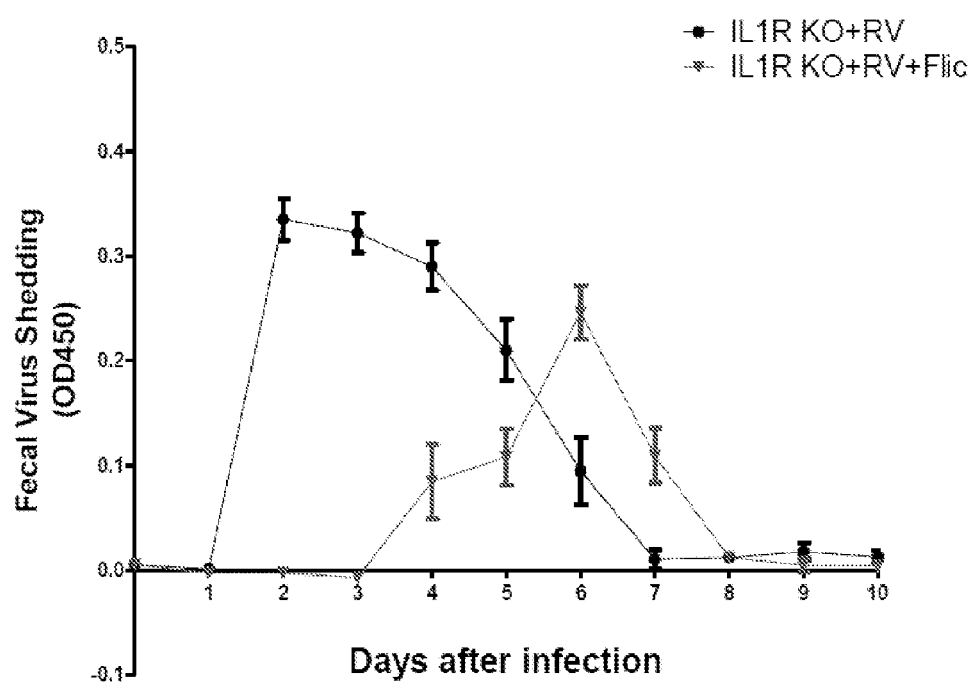
Figure 14:
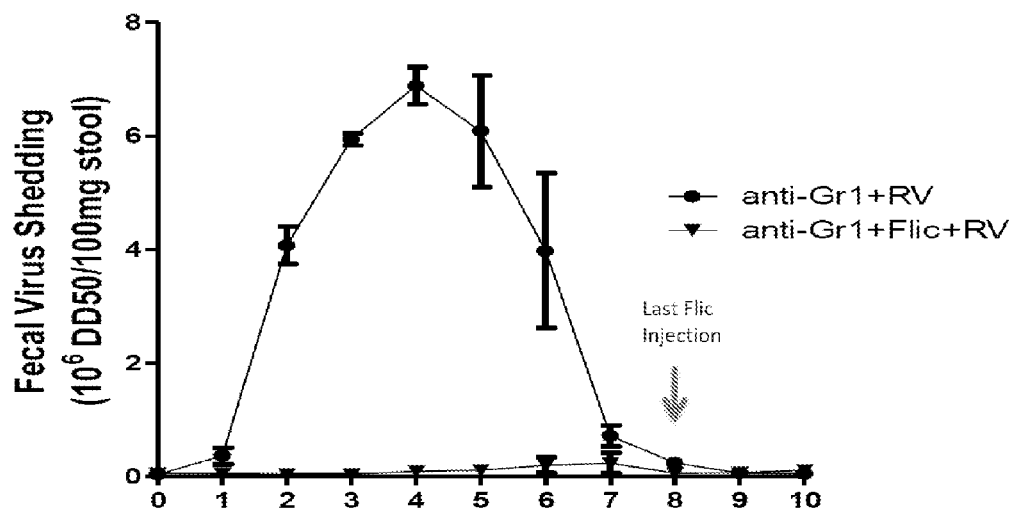
FIG. 14 shows data suggesting flagellin (FliC) protects anti-Gr1-treated mice from murine rotavirus infection. Monoclonal antibody [mAb-anti-granulocyte receptor 1 (Gr-1)] depletes neutrophils in murine models of infection.
Figure 15:
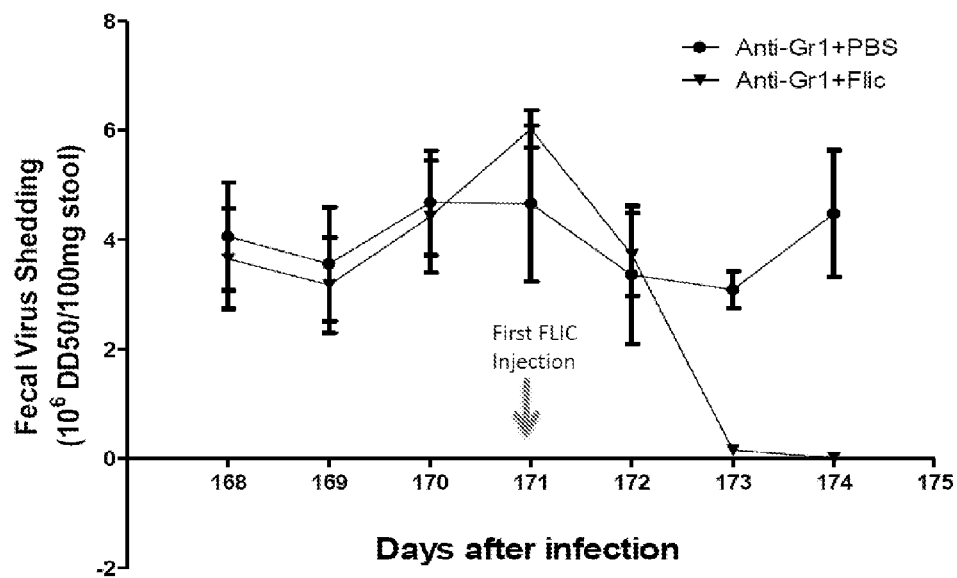
FIG. 15 shows data suggesting flagellin (FliC) cures chronic murine rotavirus infection in neutrophil-depleted RAG1 KO mice.
Figure 16:
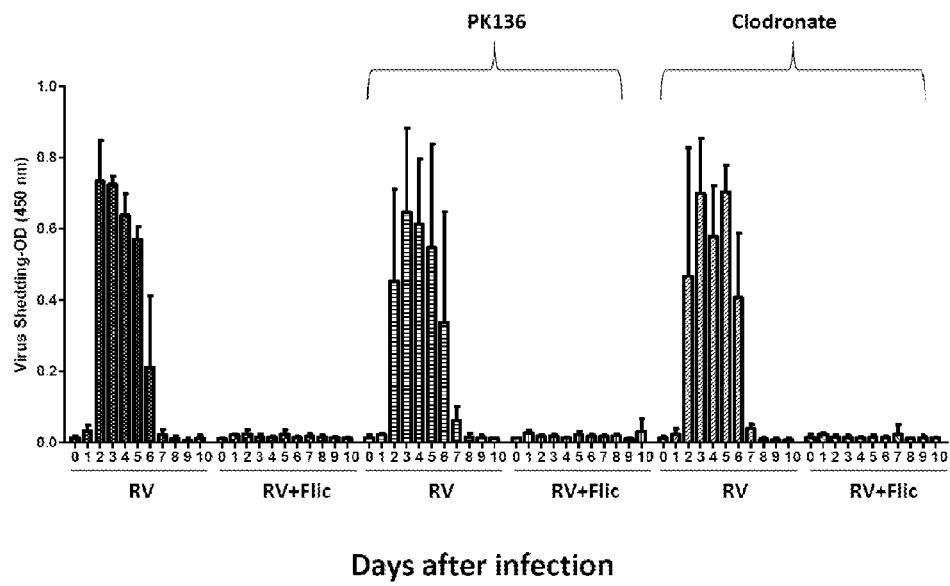
FIG. 16 shows data suggesting flagellin protects Natural Killer or Macrophage-depleted B6 mice from murine rotavirus infection.
Figure 17:
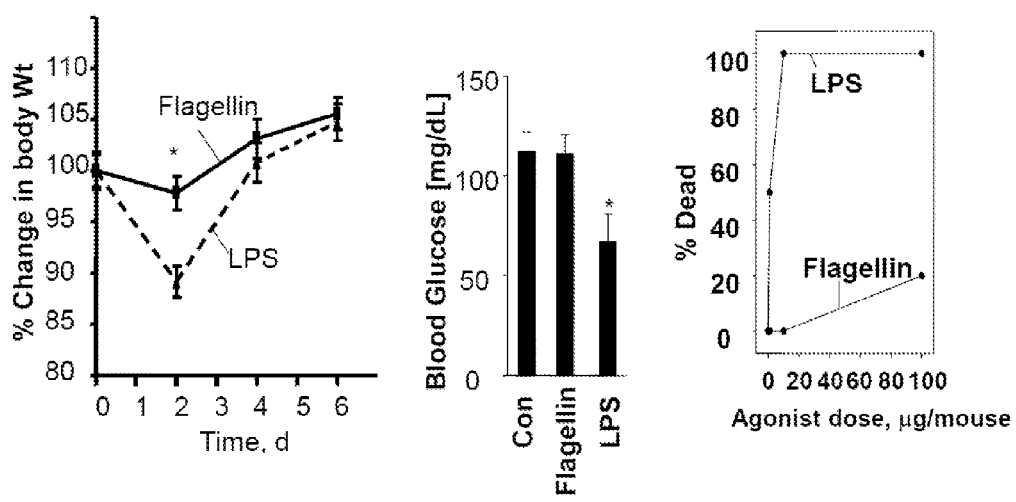
FIG. 17 shows data suggesting flagellin lacks LPS's induction of adverse events.
Figure 18:
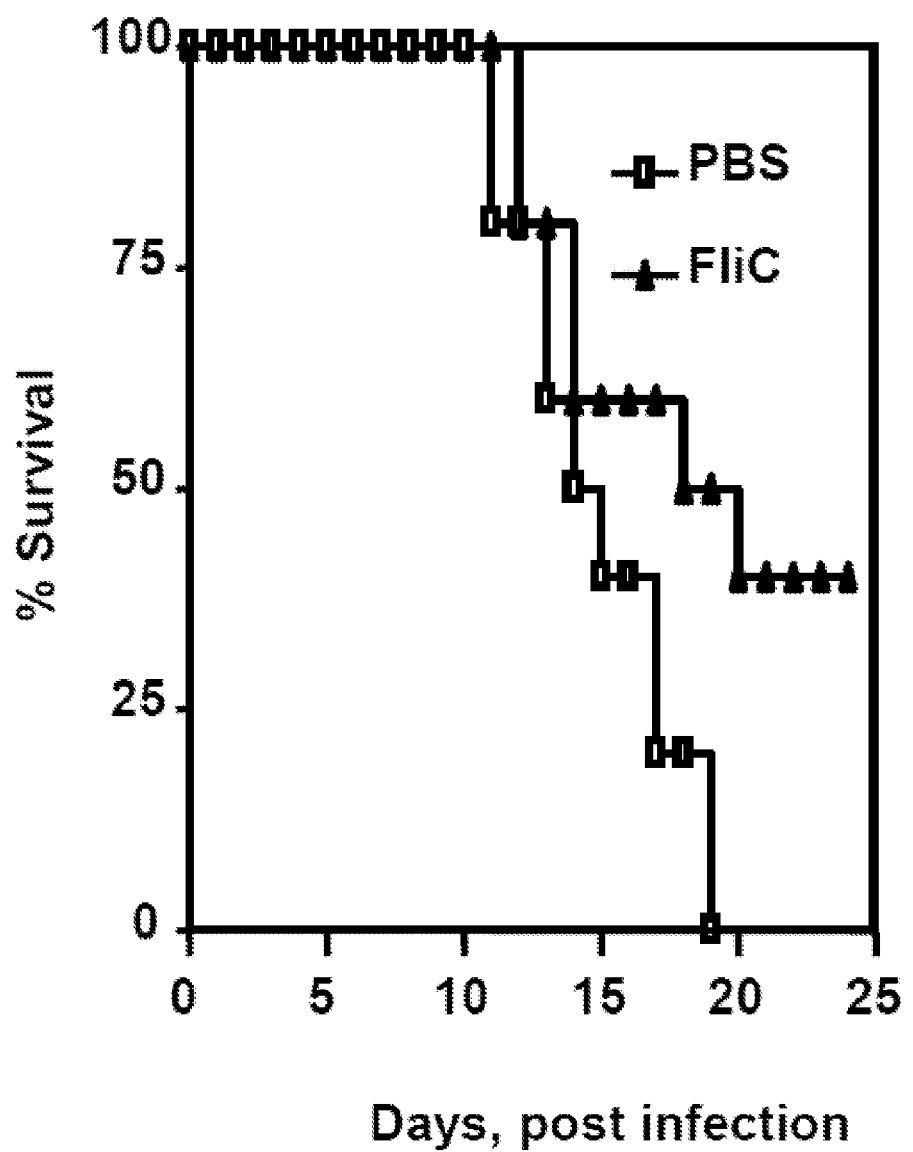
FIG. 18 shows data suggesting flagellin protects against *salmonella* infection.

TLR5-deficient mice (n=5) were orally administered buffer (PBS) or a high dose of rotavirus (RV-105× minimum shedding dose) on day 0. Some mice (RV+Flagellin), received intraperitoneal injections of flagellin (20 mg/mouse) on days 0, 2, and 4. In FIG. 8, viral infectivity is indicated by degree of viral antigens in feces, which is measured by ELISA. This experiment shows that, in TLR5-deficient mice, prophylactic treatment with flagellin did not protect mice from RV infection but merely delayed the course of infection by a few days.

---

The invention claimed is:

1. A method of treating a viral infection comprising administering an isolated flagellin in an effective amount to activate TLR5 to subject that is diagnosed with, suspected of, or exhibiting symptoms of a viral infection wherein the isolated flagellin is administered in the absence of administering a viral vaccine comprising viral nucleic acid or viral antigen.

2. The method of claim 1, wherein the isolated flagellin comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, or SEQ ID NO: 12.

3. The method of claim 1, wherein the subject is a human.

4. The method of claim 1, wherein isolated flagellin is administered in combination with a second antiviral agent.

5. The method of claim 1, wherein isolated flagellin is administered in combination with abacavir, acyclovir, adefovir, amantadine, amprenavir, rintatolimod, umifenovir, atazanavir, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, tromantadine, valaciclovir, valganciclovir, vicriviroc, vidarabine, viramidine zalcitabine, zanamivir, and/or zidovudine.

6. The method of claim 1, wherein the subject has a compromised immune system.

7. The method of claim 1, wherein the subject is an organ transplant recipient, undergoing hemodialysis, diagnosed with cancer, receiving an immunosuppressive drug, or diagnosed with an HIV-infection.

8. A pharmaceutical composition comprising an isolated flagellin and a second antiviral agent wherein the second antiviral agent is selected from abacavir, acyclovir, adefovir, amantadine, amprenavir, rintatolimod, umifenovir, atazanavir, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, tromantadine, valaciclovir, valganciclovir, vicriviroc, vidarabine, viramidine zalcitabine, zanamivir, and zidovudine.

9. A pharmaceutical composition comprising an isolated flagellin and efavirenz, emtricitabine, and tenofovir disoproxil.

10. A pharmaceutical composition comprising an isolated flagellin and abacavir, lamivudine, and zidovudine.

11. A pharmaceutical composition comprising an isolated flagellin and emtricitabine and tenofovir disoproxil.

12. The method of claim 1, wherein the isolated flagellin is administered in combination with efavirenz, emtricitabine and tenofovir disoproxil.

13. The method of claim 1, wherein the isolated flagellin is administered in combination with abacavir, lamivudine, and zidovudine.

14. The method of claim 1, wherein isolated flagellin is administered in combination with emtricitabine and tenofovir disoproxil.

15. The method of claim 1, wherein the subject is diagnosed with a rotaviral infection.

16. The method of claim 1, wherein the subject is diagnosed with an influenza viral infection.

* * * * *

```
                      SEQUENCE LISTING

<160> NUMBER OF SEQ ID NOS: 12

<210> SEQ ID NO 1
<211> LENGTH: 495
<212> TYPE: PRT
<213> ORGANISM: Salmonella typhimurium

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Thr Leu Asn Val Gln
                165                 170                 175

Gln Lys Tyr Lys Val Ser Asp Thr Ala Ala Thr Val Thr Gly Tyr Ala
            180                 185                 190

Asp Thr Thr Ile Ala Leu Asp Asn Ser Thr Phe Lys Ala Ser Ala Thr
        195                 200                 205

Gly Leu Gly Gly Thr Asp Gln Lys Ile Asp Gly Asp Leu Lys Phe Asp
    210                 215                 220

Asp Thr Thr Gly Lys Tyr Tyr Ala Lys Val Thr Val Thr Gly Gly Thr
225                 230                 235                 240
```

```
Gly Lys Asp Gly Tyr Tyr Glu Val Ser Val Asp Lys Thr Asn Gly Glu
            245                 250                 255
Val Thr Leu Ala Gly Gly Ala Thr Ser Pro Leu Thr Gly Gly Leu Pro
            260                 265                 270
Ala Thr Ala Thr Glu Asp Val Lys Asn Val Gln Val Ala Asn Ala Asp
            275                 280                 285
Leu Thr Glu Ala Lys Ala Ala Leu Thr Ala Ala Gly Val Thr Gly Thr
290                 295                 300
Ala Ser Val Val Lys Met Ser Tyr Thr Asp Asn Asn Gly Lys Thr Ile
305                 310                 315                 320
Asp Gly Gly Leu Ala Val Lys Val Gly Asp Tyr Tyr Ser Ala Thr
            325                 330                 335
Gln Asn Lys Asp Gly Ser Ile Ser Ile Asn Thr Thr Lys Tyr Thr Ala
            340                 345                 350
Asp Asp Gly Thr Ser Lys Thr Ala Leu Asn Lys Leu Gly Gly Ala Asp
            355                 360                 365
Gly Lys Thr Glu Val Val Ser Ile Gly Gly Lys Thr Tyr Ala Ala Ser
            370                 375                 380
Lys Ala Glu Gly His Asn Phe Lys Ala Gln Pro Asp Leu Ala Glu Ala
385                 390                 395                 400
Ala Ala Thr Thr Thr Glu Asn Pro Leu Gln Lys Ile Asp Ala Ala Leu
            405                 410                 415
Ala Gln Val Asp Thr Leu Arg Ser Asp Leu Gly Ala Val Gln Asn Arg
            420                 425                 430
Phe Asn Ser Ala Ile Thr Asn Leu Gly Asn Thr Val Asn Asn Leu Thr
            435                 440                 445
Ser Ala Arg Ser Arg Ile Glu Asp Ser Asp Tyr Ala Thr Glu Val Ser
450                 455                 460
Asn Met Ser Arg Ala Gln Ile Leu Gln Gln Ala Gly Thr Ser Val Leu
465                 470                 475                 480
Ala Gln Ala Asn Gln Val Pro Gln Asn Val Leu Ser Leu Leu Arg
            485                 490                 495

<210> SEQ ID NO 2
<211> LENGTH: 506
<212> TYPE: PRT
<213> ORGANISM: Salmonella typhimurium

<400> SEQUENCE: 2

Met Ala Gln Val Ile Asn Thr Asn Ser Leu Ser Leu Leu Thr Gln Asn
1               5                   10                  15
Asn Leu Asn Lys Ser Gln Ser Ala Leu Gly Thr Ala Ile Glu Arg Leu
            20                  25                  30
Ser Ser Gly Leu Arg Ile Asn Ser Ala Lys Asp Asp Ala Ala Gly Gln
        35                  40                  45
Ala Ile Ala Asn Arg Phe Thr Ala Asn Ile Lys Gly Leu Thr Gln Ala
    50                  55                  60
Ser Arg Asn Ala Asn Asp Gly Ile Ser Ile Ala Gln Thr Thr Glu Gly
65                  70                  75                  80
Ala Leu Asn Glu Ile Asn Asn Leu Gln Arg Val Arg Glu Leu Ala
            85                  90                  95
Val Gln Ser Ala Asn Ser Thr Asn Ser Gln Ser Asp Leu Asp Ser Ile
            100                 105                 110
Gln Ala Glu Ile Thr Gln Arg Leu Asn Glu Ile Asp Arg Val Ser Gly
```

```
            115                 120                 125
Gln Thr Gln Phe Asn Gly Val Lys Val Leu Ala Gln Asp Asn Thr Leu
        130                 135                 140
Thr Ile Gln Val Gly Ala Asn Asp Gly Glu Thr Ile Asp Ile Asp Leu
145                 150                 155                 160
Lys Gln Ile Asn Ser Gln Thr Leu Gly Leu Asp Ser Leu Asn Val Gln
                165                 170                 175
Lys Ala Tyr Asp Val Lys Asp Thr Ala Val Thr Thr Lys Ala Tyr Ala
            180                 185                 190
Asn Asn Gly Thr Thr Leu Asp Val Ser Gly Leu Asp Asp Ala Ala Ile
        195                 200                 205
Lys Ala Ala Thr Gly Gly Thr Asn Gly Thr Ala Ser Val Thr Gly Gly
210                 215                 220
Ala Val Lys Phe Asp Ala Asp Asn Lys Tyr Phe Val Thr Ile Gly
225                 230                 235                 240
Gly Phe Thr Gly Ala Asp Ala Ala Lys Asn Gly Asp Tyr Glu Val Asn
                245                 250                 255
Val Ala Thr Asp Gly Thr Val Thr Leu Ala Ala Gly Ala Thr Lys Thr
            260                 265                 270
Thr Met Pro Ala Gly Ala Thr Thr Lys Thr Glu Val Gln Glu Leu Lys
        275                 280                 285
Asp Thr Pro Ala Val Val Ser Ala Asp Ala Lys Asn Ala Leu Ile Ala
        290                 295                 300
Gly Gly Val Asp Ala Thr Asp Ala Asn Gly Ala Glu Leu Val Lys Met
305                 310                 315                 320
Ser Tyr Thr Asp Lys Asn Gly Lys Thr Ile Glu Gly Gly Tyr Ala Leu
                325                 330                 335
Lys Ala Gly Asp Lys Tyr Tyr Ala Ala Asp Tyr Asp Glu Ala Thr Gly
            340                 345                 350
Ala Ile Lys Ala Lys Thr Thr Ser Tyr Thr Ala Ala Asp Gly Thr Thr
        355                 360                 365
Lys Thr Ala Ala Asn Gln Leu Gly Gly Val Asp Gly Lys Thr Glu Val
        370                 375                 380
Val Thr Ile Asp Gly Lys Thr Tyr Asn Ala Ser Lys Ala Ala Gly His
385                 390                 395                 400
Asp Phe Lys Ala Gln Pro Glu Leu Ala Glu Ala Ala Lys Thr Thr
                405                 410                 415
Glu Asn Pro Leu Gln Lys Ile Asp Ala Ala Leu Ala Gln Val Asp Ala
            420                 425                 430
Leu Arg Ser Asp Leu Gly Ala Val Gln Asn Arg Phe Asn Ser Ala Ile
        435                 440                 445
Thr Asn Leu Gly Asn Thr Val Asn Asn Leu Ser Glu Ala Arg Ser Arg
        450                 455                 460
Ile Glu Asp Ser Asp Tyr Ala Thr Glu Val Ser Asn Met Ser Arg Ala
465                 470                 475                 480
Gln Ile Leu Gln Gln Ala Gly Thr Ser Val Leu Ala Gln Ala Asn Gln
                485                 490                 495
Val Pro Gln Asn Val Leu Ser Leu Leu Arg
            500                 505

<210> SEQ ID NO 3
<211> LENGTH: 398
<212> TYPE: PRT
<213> ORGANISM: Salmonella typhimurium
```

<400> SEQUENCE: 3

```
Phe Thr Ala Asn Ile Lys Gly Leu Thr Gln Ala Ser Arg Asn Ala Asn
1               5                   10                  15

Asp Gly Ile Ser Ile Ala Gln Thr Thr Glu Gly Ala Leu Asn Glu Ile
            20                  25                  30

Asn Asn Asn Leu Gln Arg Val Arg Glu Leu Ala Val Gln Ser Ala Asn
        35                  40                  45

Ser Thr Asn Ser Gln Ser Asp Leu Asp Ser Ile Gln Ala Glu Ile Thr
    50                  55                  60

Gln Arg Leu Asn Glu Ile Asp Arg Val Ser Gly Gln Thr Gln Phe Asn
65                  70                  75                  80

Gly Val Lys Val Leu Ala Gln Asp Asn Thr Leu Thr Ile Gln Val Gly
                85                  90                  95

Ala Asn Asp Gly Glu Thr Ile Asp Ile Asp Leu Lys Gln Ile Asn Ser
            100                 105                 110

Gln Thr Leu Gly Leu Asp Thr Leu Asn Val Gln Gln Lys Tyr Lys Val
        115                 120                 125

Ser Asp Thr Ala Ala Thr Val Thr Gly Tyr Ala Asp Thr Thr Ile Ala
    130                 135                 140

Leu Asp Asn Ser Thr Phe Lys Ala Ser Ala Thr Gly Leu Gly Gly Thr
145                 150                 155                 160

Asp Gln Lys Ile Asp Gly Asp Leu Lys Phe Asp Asp Thr Thr Gly Lys
                165                 170                 175

Tyr Tyr Ala Lys Val Thr Val Thr Gly Thr Gly Lys Asp Gly Tyr
            180                 185                 190

Tyr Glu Val Ser Val Asp Lys Thr Asn Gly Glu Val Thr Leu Ala Gly
        195                 200                 205

Gly Ala Thr Ser Pro Leu Thr Gly Gly Leu Pro Ala Thr Ala Thr Glu
    210                 215                 220

Asp Val Lys Asn Val Gln Val Ala Asn Ala Asp Leu Thr Glu Ala Lys
225                 230                 235                 240

Ala Ala Leu Thr Ala Ala Gly Val Thr Gly Thr Ala Ser Val Val Lys
                245                 250                 255

Met Ser Tyr Thr Asp Asn Asn Gly Lys Thr Ile Asp Gly Gly Leu Ala
            260                 265                 270

Val Lys Val Gly Asp Asp Tyr Tyr Ser Ala Thr Gln Asn Lys Asp Gly
        275                 280                 285

Ser Ile Ser Ile Asn Thr Thr Lys Tyr Thr Ala Asp Asp Gly Thr Ser
    290                 295                 300

Lys Thr Ala Leu Asn Lys Leu Gly Gly Ala Asp Gly Lys Thr Glu Val
305                 310                 315                 320

Val Ser Ile Gly Gly Lys Thr Tyr Ala Ala Ser Lys Ala Glu Gly His
                325                 330                 335

Asn Phe Lys Ala Gln Pro Asp Leu Ala Glu Ala Ala Thr Thr Thr
            340                 345                 350

Glu Asn Pro Leu Gln Lys Ile Asp Ala Ala Leu Ala Gln Val Asp Thr
        355                 360                 365

Leu Arg Ser Asp Leu Ala Ala Val Gln Asn Arg Phe Asn Ser Ala Ile
    370                 375                 380

Thr Asn Leu Gly Asn Thr Val Asn Asn Leu Thr Ser Ala Arg
385                 390                 395
```

```
<210> SEQ ID NO 4
<211> LENGTH: 290
<212> TYPE: PRT
<213> ORGANISM: Salmonella typhimurium

<400> SEQUENCE: 4

Met Ala Leu Thr Val Asn Thr Asn Ile Ala Ser Leu Asn Thr Gln Arg
1               5                   10                  15

Asn Leu Asn Asn Ser Ser Ala Ser Leu Asn Thr Ser Leu Gln Arg Leu
            20                  25                  30

Ser Thr Gly Ser Arg Ile Asn Ser Ala Lys Asp Asp Ala Ala Gly Leu
        35                  40                  45

Gln Ile Ala Asn Arg Leu Thr Ser Gln Val Asn Gly Leu Asn Val Ala
    50                  55                  60

Thr Lys Asn Ala Asn Asp Gly Ile Ser Leu Ala Gln Thr Ala Glu Gly
65                  70                  75                  80

Ala Leu Gln Gln Ser Thr Asn Ile Leu Gln Arg Met Arg Asp Leu Ser
                85                  90                  95

Leu Gln Ser Ala Asn Gly Ser Asn Ser Asp Ser Glu Arg Thr Ala Leu
            100                 105                 110

Asn Gly Glu Val Lys Gln Leu Gln Lys Glu Leu Asp Arg Ile Ser Asn
        115                 120                 125

Thr Thr Thr Phe Gly Gly Arg Lys Leu Leu Asp Gly Ser Phe Gly Val
    130                 135                 140

Ala Ser Phe Gln Val Gly Ser Ala Ala Asn Glu Ile Ile Ser Val Gly
145                 150                 155                 160

Ile Gly Gly Gly Lys Leu Met Ile Lys Leu Lys Phe Gly Val Phe Phe
                165                 170                 175

Thr Val Leu Leu Ser Ser Ala Tyr Ala His Gly Thr Pro Gln Asn Ile
            180                 185                 190

Thr Asp Leu Cys Ala Glu Tyr His Asn Thr Gln Ile His Thr Leu Asn
        195                 200                 205

Asp Lys Ile Phe Ser Tyr Thr Glu Ser Leu Ala Gly Lys Arg Glu Met
    210                 215                 220

Ala Ile Ile Thr Phe Lys Asn Gly Ala Thr Phe Gln Val Glu Val Pro
225                 230                 235                 240

Gly Ser Gln His Ile Asp Ser Gln Lys Lys Ala Ile Glu Arg Met Lys
                245                 250                 255

Asp Thr Leu Arg Ile Ala Tyr Leu Thr Glu Ala Lys Val Glu Lys Leu
            260                 265                 270

Cys Val Trp Asn Asn Lys Thr Pro His Ala Ile Ala Ala Ile Ser Met
        275                 280                 285

Ala Asn
    290

<210> SEQ ID NO 5
<211> LENGTH: 39
<212> TYPE: PRT
<213> ORGANISM: Salmonella typhimurium

<400> SEQUENCE: 5

Gly Ala Leu Asn Glu Ile Asn Asn Asn Leu Gln Arg Val Arg Glu Leu
1               5                   10                  15

Ala Val Gln Ser Ala Asn Ser Thr Asn Ser Gln Ser Asp Leu Asp Ser
            20                  25                  30

Ile Gln Ala Glu Ile Thr Gln
```

<210> SEQ ID NO 6
<211> LENGTH: 44
<212> TYPE: PRT
<213> ORGANISM: Salmonella typhimurium

<400> SEQUENCE: 6

Thr Gln Phe Ser Gly Val Lys Val Leu Ala Gln Asp Asn Thr Leu Thr
1               5                   10                  15

Ile Gln Val Gly Ala Asn Asp Gly Glu Thr Ile Asp Ile Asp Leu Lys
            20                  25                  30

Gln Ile Asn Ser Gln Thr Leu Gly Leu Asp Thr Leu
        35                  40

<210> SEQ ID NO 7
<211> LENGTH: 50
<212> TYPE: PRT
<213> ORGANISM: Salmonella typhimurium

<400> SEQUENCE: 7

Glu Gly Ala Leu Asn Glu Ile Asn Asn Leu Gln Arg Val Arg Glu
1               5                   10                  15

Leu Ala Val Gln Ser Ala Asn Ser Thr Asn Ser Gln Ser Asp Leu Asp
            20                  25                  30

Ser Ile Gln Ala Glu Ile Thr Gln Arg Leu Asn Glu Ile Asp Arg Val
        35                  40                  45

Asn Gly
    50

<210> SEQ ID NO 8
<211> LENGTH: 98
<212> TYPE: PRT
<213> ORGANISM: Salmonella typhimurium

<400> SEQUENCE: 8

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Phe Thr Ala Asn Ile Lys Gly Leu Thr Gln Ala Ser
    50                  55                  60

Arg Asn Ala Asn Asp Gly Ile Ser Ile Ala Gln Thr Thr Glu Gly Ala
65                  70                  75                  80

Leu Asn Glu Ile Asn Asn Asn Leu Gln Arg Val Arg Glu Leu Ala Val
                85                  90                  95

Gln Ser

<210> SEQ ID NO 9
<211> LENGTH: 32
<212> TYPE: PRT
<213> ORGANISM: Salmonella typhimurium

<400> SEQUENCE: 9

Leu Gln Lys Ile Asp Ala Ala Leu Ala Gln Val Asp Thr Leu Arg Ser
1               5                   10                  15

Asp Leu Gly Ala Val Gln Asn Arg Phe Asn Ser Ala Ile Thr Asn Leu

<210> SEQ ID NO 10
<211> LENGTH: 29
<212> TYPE: PRT
<213> ORGANISM: Salmonella typhimurium

<400> SEQUENCE: 10

```
Thr Leu Arg Ser Asp Leu Gly Ala Val Gln Asn Arg Phe Asn Ser Ala
1               5                   10                  15

Ile Thr Asn Leu Gly Asn Thr Val Asn Asn Leu Ser Ser
            20                  25
```

<210> SEQ ID NO 11
<211> LENGTH: 51
<212> TYPE: PRT
<213> ORGANISM: Salmonella typhimurium

<400> SEQUENCE: 11

```
Glu Gln Ala Ala Lys Thr Thr Glu Asn Pro Leu Gln Lys Ile Asp Ala
1               5                   10                  15

Ala Leu Ala Gln Val Asp Thr Leu Arg Ser Asp Leu Gly Ala Val Gln
            20                  25                  30

Asn Arg Phe Asn Ser Ala Ile Thr Asn Leu Gly Asn Thr Val Asn Asn
        35                  40                  45

Leu Ser Ser
    50
```

<210> SEQ ID NO 12
<211> LENGTH: 984
<212> TYPE: PRT
<213> ORGANISM: Salmonella typhimurium
<220> FEATURE:
<221> NAME/KEY: MISC_FEATURE
<223> OTHER INFORMATION: GAG = GLU
<220> FEATURE:
<221> NAME/KEY: MISC_FEATURE
<223> OTHER INFORMATION: CTT = LEU
<220> FEATURE:
<221> NAME/KEY: MISC_FEATURE
<223> OTHER INFORMATION: CCG = PRO

<400> SEQUENCE: 12

```
Met Glu Thr Ala Arg Gly Gly Leu Tyr Ser Glu Arg His Ile Ser His
1               5                   10                  15

Ile Ser His Ile Ser His Ile Ser His Ile Ser His Ile Ser Gly Leu
            20                  25                  30

Tyr Met Glu Thr Ala Leu Ala Ser Glu Arg Met Glu Thr Thr His Arg
        35                  40                  45

Gly Leu Tyr Gly Leu Asn Gly Leu Asn Met Glu Thr Gly Leu Tyr Ala
    50                  55                  60

Arg Gly Ala Ser Pro Cys Thr Thr Thr Tyr Arg Ala Ser Pro Ala Ser
65                  70                  75                  80

Pro Ala Ser Pro Ala Ser Pro Leu Tyr Ser Ala Ser Pro Cys Cys Gly
            85                  90                  95

Met Glu Thr Ala Leu Ala Gly Leu Asn Val Ala Leu Ile Leu Glu Ala
            100                 105                 110

Ser Asn Thr His Arg Ala Ser Asn Ser Glu Arg Cys Thr Thr Ser Glu
        115                 120                 125

Arg Cys Thr Thr Cys Thr Thr Thr His Arg Gly Leu Asn Ala Ser Asn
    130                 135                 140
```

```
Ala Ser Asn Cys Thr Thr Ala Ser Asn Leu Tyr Ser Ser Glu Arg Gly
145                 150                 155                 160

Leu Asn Ser Glu Arg Ser Glu Arg Cys Thr Thr Ser Glu Arg Ser Glu
                165                 170                 175

Arg Ala Leu Ala Ile Leu Glu Gly Ala Gly Ala Arg Gly Cys Thr Thr
                180                 185                 190

Ser Glu Arg Ser Glu Arg Gly Leu Tyr Cys Thr Thr Ala Arg Gly Ile
                195                 200                 205

Leu Glu Ala Ser Asn Ser Glu Arg Ala Leu Ala Leu Tyr Ser Ala Ser
210                 215                 220

Pro Ala Ser Pro Ala Leu Ala Ala Leu Ala Gly Leu Tyr Gly Leu Asn
225                 230                 235                 240

Ala Leu Ala Ile Leu Glu Ala Leu Ala Ala Ser Asn Ala Arg Gly Pro
                245                 250                 255

His Glu Thr His Arg Ser Glu Arg Ala Ser Asn Ile Leu Glu Leu Tyr
                260                 265                 270

Ser Gly Leu Tyr Cys Thr Thr His Arg Gly Leu Asn Ala Leu Ala
                275                 280                 285

Ser Glu Arg Ala Arg Gly Ala Ser Asn Ala Leu Ala Ala Ser Asn Ala
290                 295                 300

Ser Pro Gly Leu Tyr Ile Leu Glu Ser Glu Arg Ile Leu Glu Ala Leu
305                 310                 315                 320

Ala Gly Leu Asn Thr His Arg Thr His Arg Gly Ala Gly Gly Leu Tyr
                325                 330                 335

Ala Leu Ala Cys Thr Thr Ala Ser Asn Gly Ala Gly Ile Leu Glu Ala
                340                 345                 350

Ser Asn Ala Ser Asn Ala Ser Asn Cys Thr Thr Gly Leu Asn Ala Arg
                355                 360                 365

Gly Val Ala Leu Ala Arg Gly Gly Ala Gly Cys Thr Thr Ser Glu Arg
    370                 375                 380

Val Ala Leu Gly Leu Asn Ala Leu Ala Thr His Arg Ala Ser Asn Gly
385                 390                 395                 400

Leu Tyr Thr His Arg Ala Ser Asn Ser Glu Arg Ala Ser Pro Ser Glu
                405                 410                 415

Arg Ala Ser Pro Cys Thr Thr Leu Tyr Ser Ser Glu Arg Ile Leu Glu
                420                 425                 430

Gly Leu Asn Ala Ser Pro Gly Ala Gly Ile Leu Glu Gly Leu Asn Gly
                435                 440                 445

Leu Asn Ala Arg Gly Cys Thr Thr Gly Ala Gly Gly Ala Gly Ile Leu
                450                 455                 460

Glu Ala Ser Pro Ala Arg Gly Val Ala Leu Ser Glu Arg Ala Ser Asn
465                 470                 475                 480

Gly Leu Asn Thr His Arg Gly Leu Asn Pro His Glu Ala Ser Asn Gly
                485                 490                 495

Leu Tyr Val Ala Leu Leu Tyr Ser Val Ala Leu Cys Thr Thr Ser Glu
                500                 505                 510

Arg Gly Leu Asn Ala Ser Pro Ala Ser Asn Gly Leu Asn Met Glu Thr
                515                 520                 525

Leu Tyr Ser Ile Leu Glu Gly Leu Asn Val Ala Leu Gly Leu Tyr Ala
                530                 535                 540

Leu Ala Ala Ser Asn Ala Ser Pro Gly Leu Tyr Gly Ala Gly Thr His
545                 550                 555                 560
```

```
Arg Ile Leu Glu Thr His Arg Ile Leu Glu Ala Ser Pro Cys Thr Thr
                565                 570                 575

Gly Leu Asn Leu Tyr Ser Ile Leu Glu Ala Ser Pro Val Ala Leu Leu
            580                 585                 590

Tyr Ser Ser Glu Arg Cys Thr Thr Gly Leu Tyr Cys Thr Thr Ala Ser
        595                 600                 605

Pro Gly Leu Tyr Pro His Glu Ala Ser Asn Val Ala Leu Ala Ser Asn
    610                 615                 620

Ser Glu Arg Cys Cys Gly Gly Leu Tyr Ile Leu Glu Ser Glu Arg Gly
625                 630                 635                 640

Leu Tyr Gly Leu Tyr Gly Leu Tyr Gly Leu Tyr Gly Leu Tyr Ile Leu
                645                 650                 655

Glu Cys Thr Thr Ala Ser Pro Ser Glu Arg Met Glu Thr Gly Leu Tyr
                660                 665                 670

Thr His Arg Cys Thr Thr Ile Leu Glu Ala Ser Asn Gly Ala Gly Ala
            675                 680                 685

Ser Pro Ala Leu Ala Ala Leu Ala Ala Leu Ala Ala Leu Ala Leu Tyr
        690                 695                 700

Ser Leu Tyr Ser Ser Glu Arg Thr His Arg Ala Leu Ala Ala Ser Asn
705                 710                 715                 720

Cys Cys Gly Cys Thr Thr Ala Leu Ala Ser Glu Arg Ile Leu Glu Ala
                725                 730                 735

Ser Pro Ser Glu Arg Ala Leu Ala Cys Thr Thr Ser Glu Arg Leu Tyr
            740                 745                 750

Ser Val Ala Leu Ala Ser Pro Ala Leu Ala Val Ala Leu Ala Arg Gly
            755                 760                 765

Ser Glu Arg Ser Glu Arg Cys Thr Thr Gly Leu Tyr Ala Leu Ala Ile
            770                 775                 780

Leu Glu Gly Leu Asn Ala Ser Asn Ala Arg Gly Pro His Glu Ala Ser
785                 790                 795                 800

Pro Ser Glu Arg Ala Leu Ala Ile Leu Glu Thr His Arg Ala Ser Asn
                805                 810                 815

Cys Thr Thr Gly Leu Tyr Ala Ser Asn Thr His Arg Val Ala Leu Thr
                820                 825                 830

His Arg Ala Ser Asn Cys Thr Thr Ala Ser Asn Ser Glu Arg Ala Leu
            835                 840                 845

Ala Ala Arg Gly Ser Glu Arg Ala Arg Gly Ile Leu Glu Gly Ala Gly
            850                 855                 860

Ala Ser Pro Ala Leu Ala Ala Ser Pro Thr Tyr Arg Ala Leu Ala Thr
865                 870                 875                 880

His Arg Gly Ala Gly Val Ala Leu Ser Glu Arg Ala Ser Asn Met Glu
                885                 890                 895

Thr Ser Glu Arg Leu Tyr Ser Ala Leu Ala Gly Leu Asn Ile Leu Glu
            900                 905                 910

Cys Thr Thr Gly Leu Asn Gly Leu Asn Ala Leu Ala Gly Leu Tyr Thr
            915                 920                 925

His Arg Ser Glu Arg Val Ala Leu Cys Thr Thr Ala Leu Ala Gly Leu
            930                 935                 940
```

```
Asn Ala Leu Ala Ala Ser Asn Gly Leu Asn Val Ala Leu Cys Cys Gly
945                 950                 955                 960

Gly Leu Asn Ala Ser Asn Val Ala Leu Cys Thr Thr Ser Glu Arg Cys
                965                 970                 975

Thr Thr Cys Thr Thr Ala Arg Gly
            980
```